(12) United States Patent
Pasche

(10) Patent No.: US 8,492,096 B2
(45) Date of Patent: Jul. 23, 2013

(54) TGFBR1 EXPRESSION MODIFIES RISK FOR COLORECTAL CANCER

(76) Inventor: Boris Pasche, Chicago, IL (US)

(*) Notice: Subject to any disclaimer, the term of this patent is extended or adjusted under 35 U.S.C. 154(b) by 0 days.

(21) Appl. No.: 12/647,207

(22) Filed: Dec. 24, 2009

(65) Prior Publication Data

US 2010/0267028 A1    Oct. 21, 2010

Related U.S. Application Data

(60) Provisional application No. 61/140,758, filed on Dec. 24, 2008.

(51) Int. Cl.
*C12Q 1/68* (2006.01)

(52) U.S. Cl.
USPC .......... 435/6.14; 435/6.1; 435/6.11; 435/6.18

(58) Field of Classification Search
None
See application file for complete search history.

(56) References Cited

U.S. PATENT DOCUMENTS

2005/0282207 A1* 12/2005 Rokutan et al. .................. 435/6
2008/0064049 A1*  3/2008 Clarke et al. ................. 435/7.23

FOREIGN PATENT DOCUMENTS

WO    WO 2010/019690    *    2/2010

OTHER PUBLICATIONS

Lu, Zhao et al. Presence of two signaling TGFB receptors in human pancreatic cancer correlates with advanced tumor state. 1997 Digestive Diseases and Sciences. vol. 42 No. 10 pp. 2054-2063.*
Abou-Shady, Mohamed et al. Transforming Growth Factor Betas and Their Signaling Receptors in Human Hepatocellular Carcinoma. 1999 Am J Surg. vol. 177 pp. 209-2015.*
Hoshikawa, Yasushit et al. Hypoxia induces different genes in the lungs of rats compared with mice. Physical Genomics 2003 vol. 12 pp. 209-219.*
Whitehead, Andrew et al. Variation in tissue specific gene expression among natural populations. Genome Biology 2005 vol. 6 Issue 2 Article R13.*
Chan, Eric. Integrating Transcriptomics and Proteomics. G&P magazine 2006 vol. 6 No. 3 pp. 20-26.*
Cheung, Vivian et al. Natural variation in human gene expression assessed in lymphoblastoid cells. Nature Genetics 2003 vol. 33 pp. 422-425.*
Valle, Laura et al. Germline allele specific expression of TGFBR1 confers an increased risk of colorectal cancer. Science Sep. 2008 vol. 321 pp. 1361-1365.*
Alberici et al. (2006) Oncog 25(13):1841-51, "Smad4 haploinsufficiency in mouse models for intestinal cancer".
Becker, et al. (2004) Immunity 21(4):491-501, "TGF-β suppresses tumor progression in colon cancer by inhibition of IL-6 transsignaling".
Bian et al. (2005) J Clin Oncol 23(13):3074-8, "TGFBR1*6A May Contribute to Hereditary Colorectal Cancer".
Boivin et al. (2003) Gastroenterology 124(3):762-77.22, "Pathology of mouse models of intestinal cancer: Consensus report and recommendations".
Broderick et al. (2007) Nat Genet Nov.;39(11):1315-7, "A genome-wide association study shows that common alleles of SMAD7 influence colorectal cancer risk".
Carcamo J et al. (1995) Mol Cell Biol 15:1573-1581, "Disruption of transforming growth factor beta signaling by a mutation that prevents transphosphorylation within the receptor complex".
Chen et al. (1999) Int. J. Cancer 82:43-51, "Structural alterations of transforming growth factor-β receptor genes in human cervical carcinoma".
de la Chapelle (2009) Oncogene. 28(38):3345-8, "Genetic predisposition to human disease: allele-specific expression and low-penetrance regulatory loci".
de la Chapelle et al. (2010) J Clin Oncol Jun. 1, "Clinical Relevance of Microsatellite Instability in Colorectal Cancer".
Dong et al. (2006) Blood 107(12):4589-96, "Role of transforming growth factor-β in hematologic".
Fadloun et al. (2008) Oncogene 27:477-489, "Retinoic acid induces TGFβ-dependent autocrine fibroblast growth".
Groden et al. (1991) Cell 66(3):589-600, "Identification and characterization of the familial adenomatous polyposis coli gene".
Guda et al. (2009) Cancer Res. 69(12):4959-4961, "Infrequent detection of germline allele-specific expression of TGFBR1 in lymphoblasts and tissues of colon cancer patients".
Hinoi et al. (2007) Cancer Res 67(20):9721-9730, "Mouse Model of Colonic Adenoma-Carcinoma Progression Based on Somatic Apc Inactivation".
Hohenstein et al. (2003) Genes Chromosomes & Cancer 36(3):273-282, "Serrated adenomas and mixed polyposis caused by a splice acceptor deletion in the mouse Smad4 gene".
Howe et al. (2004) J Med Genet Jul.;41(7):484-491, "The prevalence of MADH4 and BMPR1A mutations in juvenile polyposis and absence of BMPR2, BMPR1B, and ACVR1 mutations".
Hulit et al. (2004) Molecular and Cellular Biology 24(17):7598-7611, "Cyclin D1 genetic heterozygosity regulates colonic epithelial cell differentiation and tumor number in Apc$^{Min}$ mice".
Jakowlew et al. (2000) Peptides 21(12):1831-1837, "Retinoic acid down-regulates VPAC(1) receptors and TGF-β 3 but up-regulates TGF-β 2 in lung cancer cells".
Kaklamani et al. (2005) Cancer Res 65(8):3454-3461, "Combined Genetic Assessment of Transforming Growth Factor-β Signaling Pathway Variants May Predict Breast Cancer Risk".
Kim et al. (2006) Nature 441:1015-1019, "Smad4 signalling in T cells is required for suppression of gastrointestinal cancer".
Kinzler et al. (1998) Science 280:1036-1037, "Landscaping the cancer terrain".
Kitamura et al. (2007) Nat Genet 39(4):467-475, "SMAD4-deficient intestinal tumors recruit CCR1+ myeloid cells that promote invasion".

(Continued)

*Primary Examiner* — Carla Myers
(74) *Attorney, Agent, or Firm* — Swanson & Bratschun, LLC

(57) ABSTRACT

The present invention provides methods for assessing a genetic susceptibility to cancer in a subject which includes measuring allele specific expression or presence of at-risk haplotypes of TGFBR1, where a difference in expression or the presence of at-risk haplotypes is indicative of a cancer or susceptibility to a cancer. Methods to screen for agents that modify expression of TGRBR1 are also provided.

1 Claim, 8 Drawing Sheets

OTHER PUBLICATIONS

Larsson et al. (2001) EMBO Journal 20(7):1663-1673, "Abnormal angiogenesis but intact hematopoietic potential in TGB-β type I receptor-deficient mice".

Lei et al. (2009) Cancer Res 69(17):7046-7052, "TGFBR1 Haplotypes and Risk of Non-Small-Cell Lung Cancer".

Liu et al. (1997) Proc 94(20):10669-10674, "Transforming growth factor β-induced phosphorylation of smad3 is required for growth inhibition and transcriptional induction in epithelial cells".

Massague (2004), Nature 432:298-306, "G1 cell-cycle control and cancer".

Matsuzaki (2006) Histol Histopathol 21(6):645-662, "Smad3 phosphoisoform-mediated signaling during sporadic human colorectal carcinogenesis".

Moser et al. (1990) Science 247:322-324, "A dominant mutation that predisposes to multipleintestinal neoplasia in the mouse".

Munoz et al. (2006) Cancer Res 66(20):9837-9844, "Transforming growth factor β-receptor type II inactivation induces the malignant transformation of intestinal neoplasms initiated by apc mutation".

Pasche et al. (1998) Cancer Res 58(13):2727-2732, "Type I transforming growth factor β receptor maps to 9q22 and exhibits a 20 polymorphism and a rare variant within a polyalanine tract".

Pasche et al. (1999) Cancer Res 59(22):5678-5682, "T β RI(6A) is a candidate tumor susceptibility allele".

Pasche et al. (2005) JAMA: The Journal of the American Medical Association 294(13):1634-1646, "Somatic acquisition and signaling of TGFBR1*6A in cancer".

Rosman et al. (2008) Cancer Res 68(5):1319-1328, "TGFBR1*6A enhances the migration and invasion of MCF-7 breast cancer cells through RhoA activation".

Siegel et al. (2003) Nat Rev Cancer 3(11):807-820, "Cytostatic and apoptotic actions of TGF-β in homeostasis and cancer".

Sjoblom et al. (2006) Science 314:268-274, "The consensus coding sequences of human breast and colorectal cancers".

Sodir et al. (2006) Cancer Res 66(17):8430-8438, "Smad3 deficiency promotes tumorigenesis in the distal colon of Apc$^{Min/+}$ mice".

Su et al. (1992) Science 256:668-670, "Multiple intestinal neoplasia caused by a mutation in the murine homolog of the APC gene".

Takaku et al. (1998) Cell 92(5):645-56, "Intestinal tumorigenesis in compound mutant mice of both dpc4 (Smad4) and apc genes".

Taketo et al. (2000) Cytokine & Growth Factor Reviews 11(1-2):147-57, "Gastro-intestinal tumorigenesis in Smad4 mutant mice".

Tsutsui et al. (1999) Molecular & Cellular Biology 19(10):7011-7019, "Targeted disruption of CDK4 delays cell cycle entry with enhanced p27(Kip1) activity".

Uchida et al. (2008) Curr Eye Res. 33(2):199-203, "Activation of TGF-β1 through up-regulation of TSP-1 by retinoic acid in retinal pigment epithelial cells".

Valle et al. (2008) Science 321:1361-1365, "Germline allele-specific expression of TGFBR1 confers an increased risk of colorectal cancer" DOI: 10.1126/science.1159397 Available web site www.sciencemag.org downloaded on Sep. 5, 2008.

van de Wetering et al. (2002) Cell 111: 241-250, "The β-Catenin/TCF-4 complex imposes a crypt progenitor phenotype on colorectal cancer cells".

Xie et al. (2003) Cancer J 9(4):302-312, "Loss of smad signaling in human colorectal cancer is associated with advanced disease and poor prognosis".

Xu et al. (2007) Hum Mol Genet 16(1):R14-R20, "TGF-β signaling alterations and susceptibility to colorectal cancer".

Yamagata et al. (2005) Cancer Res 65(1):157-65, "Acceleration of Smad2 and Smad3 phosphorylation via c-Jun NH2-terminal kinase during human colorectal carcinogenesis".

Yoshizawa et al. (1998) J Cell Physiol. 176(3):565-573, "Retinoids potentiate transforming growth factor-β activity in bovine endothelial cells through up-regulating the expression of transforming growth factor-β receptors".

Zawel et al. (1998) Mol Cell 1(4):611-7, "Human Smad3 and Smad4 are sequence-specific transcription activators".

Zeng et al. (2009) Cancer Res. 69(2):678-686, "Tgfbr1 haploinsufficiency is a potent modifier of colorectal cancer development".

Zhu et al. (1998) Cell 94(6):703-14, "Smad3 mutant mice develop metastatic colorectal cancer".

Pasche et al., (2010) Journal of Experimental & Clinical Cancer Research 29:57:1-6, "Constitutively decreased TGFBR1 allelic expression is a common finding in colorectal cancer and is associated with three TGFBR1 SNPs".

* cited by examiner

TGFBR1 EXPRESSION MODIFIES RISK FOR COLORECTAL CANCER

Incorporated by reference herein in its entirety is the Sequence Listing, entitled "0323_01_seq_ST25.txt," which was created Jun. 18, 2010, size 4 kilobytes.

FIELD OF THE INVENTION

The present invention relates to methods for the detection of susceptibility to and methods for treating and/or preventing cancer, including breast cancer, non small cell lung cancer, pancreatic cancer, and colorectal cancer.

BACKGROUND OF THE INVENTION

The annual worldwide influence of colorectal cancer (CRC) exceeds one million, and genes are thought to have a strong impact on CRC risk. A positive family history of CRC occurs in 20-30% of patients. Much of the predisposition to CRC remains unexplained. Aberrations in the transforming growth factor beta (TGF-beta) pathway are involved in CRC carcinogenesis, particularly mutations in TGF-beta type II receptor gene.

TGFBR1*6A, which encodes a common human TGFBR1 variant, has been previously identified and transduces TGF-β signaling less effectively than TGFBR1. Cancer risk is higher for TGFBR1*6A homozygotes than for TGFBR1*6A heterozygotes among patients with hereditary colorectal cancer and no evidence of mismatch repair deficiency. However, increased gastrointestinal tumor susceptibility has not been reported in Tgfb1+/−, Tgfbr2+/−, Smad2+/− or Smad3+/− mice, leading away from conclusions that haploinsufficiency is risk factor for cancer.

Whether haploinsufficiency of any of the TGF-β genes contributes to cancer development, including colorectal cancer development, was unknown, prior to the instant invention.

SUMMARY OF THE INVENTION

In a broad aspect, the present invention includes a method for assessing for susceptibility and/or diagnosis of cancer in a patient, comprising determining whether the individual has an allele-specific expression trait in TGFBR1 which results in decreased expression of TGFBR1. Such allele specific expression can be detected in a variety of ways known in the art, including quantitating expression level of TGFBR1, or by detecting known alleles associated with decreased expression of TGFBR1. A reduction in the expression of TGFBR1 (either of message or of protein) compared to a healthy control or an average of healthy controls is indicative of cancer, including colorectal cancer, or a predisposition or susceptibility to cancer, including colorectal cancer.

In one embodiment, the present invention includes methods by which to screen TGFBR1 alleles for determination of whether these alleles are associated with decreased expression of TGFBR1, and detecting for such alleles to detect an individual's predisposition to cancer.

The present invention also includes methods for assessing the genetic predisposition of a subject to develop cancer, including colorectal cancer. At its base, the detection method is based on the differential expression of alleles or presence of their underlying haplotypes of TGFBR1 in normal somatic cells. Differential allelic expression, in one embodiment, lowered expression, of TGFBR1 protein is indicative of a higher risk to develop colorectal cancer and other cancers. The work of the present inventor leads to the understanding that some TGFBR1 alleles (or their underlying haplotypes) are expressed at lower levels, that this expression level is heritable, and such lowered expression is more common in colorectal cancer patients than normal controls. Thus, either quantitation of expression of TGFBR1 or detection of certain alleles or underlying haplotypes that are associated with reduced expression of TGFBR1 may be used to provide information that a subject is more likely to develop colorectal or other cancers.

A method of identifying a candidate compound for modifying TGFBR1 expression, the method comprising: contacting a test compound with a cell expressing TGFBR1; monitoring expression level of TGFBR1; and selecting the test compound as a candidate compound for modifying TGFBR1 expression if the test compound modifies the expression of TGFBR1, relative to the expression of TGRBR1 in a cell of the same cell type that is not contacted with the test compound.

U.S. Ser. No. 61/088,080, first inventor: Albert de la Chapelle, entitled Allele-Specific Expression of TGFBR1 Predisposes to Colorectal Cancer, filing date Aug. 12, 2008, is incorporated by reference herein in its entirety.

BRIEF DESCRIPTION OF THE DRAWINGS

The foregoing aspects and many of the advantages of the present invention will be more readily appreciated as the same becomes better understood by reference to the following detailed description, when taken in conjunction with the accompanying drawings, wherein.

DETAILED DESCRIPTION

Figure 1:
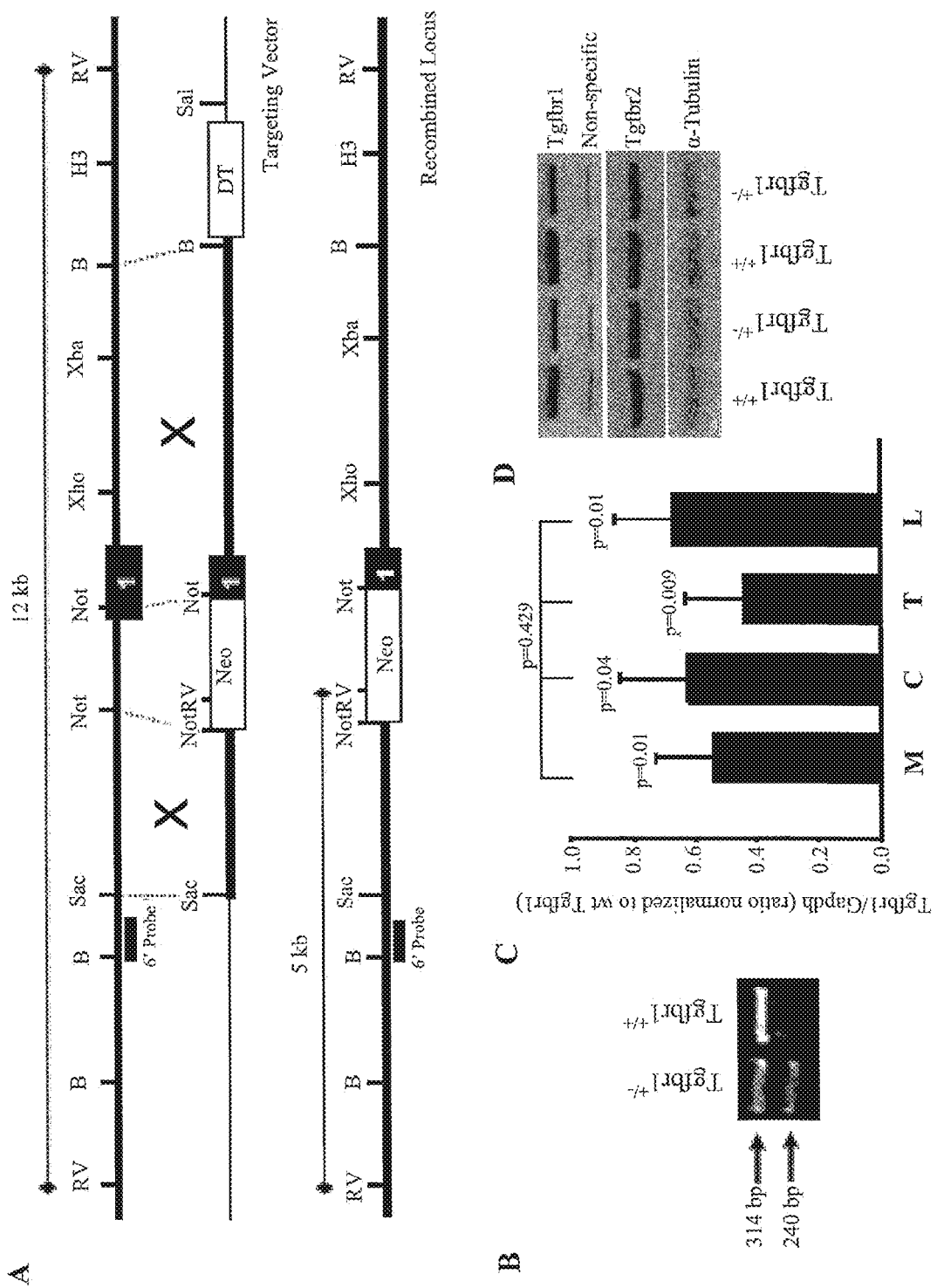
FIGS. 1A-1D show generation of a novel Tgfbr1 exon knockout mouse model.

Transforming growth factor, beta receptor 1 (TGFBR1): The protein encoded by this gene forms a heteromeric complex with type II TGF-beta receptors when bound to TGF-beta, transducing the TGF-beta signal from the cell surface to the cytoplasm. The encoded protein is a serine/threonine protein kinase. The protein is 503 amino acids; 55960 Da Interacts with CD109. The unphosphorylated protein interacts with FKBP1A and is stabilized the inactive conformation. Phosphorylation of the GS region abrogates FKBP1A binding. Interacts with SMAD2 when phosphorylated on several residues in the GS region Subcellular location: Membrane; Single-pass type I membrane protein. The accession number for the TGFBR1 gene is NM_004612. TGFBR1 gene occurs on Chromosome 9. Homo Sapiens Chromosome 9 complete sequence has a GenBank accession number NC_000009 with a total of 140273252 bp.

Haploinsufficiency occurs when a diploid organism has only a single functional copy of a gene and the single functional copy of the gene does not produce enough of a gene product (typically a protein) to bring about a wild type condition, potentially leading to an abnormal or diseased state. A haploinsufficient gene can be described as needing both alleles to be fully functional in order to express the wild type. Allele specific expression may result in haploinsufficiency.

The present inventors generated a novel Tgfbr1+/− mouse model to determine whether constitutively decreased Tgfbr1 signaling is causally involved in colorectal cancer development. When Tgfbr1+/− mice in mixed 129Svlm/C57BL/6 background were crossed with ApcMin/+ mice, a significantly higher number of tumors was observed in ApcMin/+; Tgfbr1+/− mice than in ApcMin/+; Tgfbr1+/+ mice. Surprisingly, the ApcMin/+; Tgfbr1+/− mice develop twice as many intestinal tumors as ApcMin/+; Tgfbr1+/+ mice as well as adenocarcinoma of the colon, without loss of heterozygosity at the Tgfbr1 locus. Similar results were obtained for a mouse model for breast cancer development. Data obtained in a study analyzing TGFBR1 haplotypes and risk of non-small cell lung cancer (NSCLC) also suggests that expression level of TGFBR1 is linked to occurrence of NSCLC. On the other hand, constitutive decrease of TGFBR1 expression may, rather than increase risk of cancer, may decrease risk of cancer for some cancers, including pancreatic cancer.

These results provide evidence for haploinsufficiency at the TGFBR1 locus caused by, among others, allele-specific expression of TGFBR1, can result in reduced TGFBR1-mediated TGF-β signaling. These results show that reduced TGFBR1-mediated TGF-β signaling significantly enhances colorectal cancer, breast cancer, and NSCLC development and results in increased tumor cell proliferation. These findings provide evidence for a molecular mechanism for colorectal cancer, breast cancer, and NSCLC development in individuals with constitutively altered TGFBR1 expression, a recently identified common form of human colorectal cancer, among others.

Providing further evidence for the instant invention, decreased Smad2 and Smad3 phosphorylation and increased cellular proliferation are observed in the colonic epithelium crypts of ApcMin/+; Tgfbr1+/− mice. Smad-mediated TGF-β signaling is preserved in both ApcMin/+; Tgfbr1+/+ and ApcMin/+; Tgfbr1+/− intestinal tumors, but cyclin D1 expression and cellular proliferation are significantly higher in ApcMin/+; Tgfbr1+/− tumors. Thus Tgfbr1 haploinsufficiency was associated with a small but significant decrease in TGF-β signaling mediated by decreased phosphorylation of both Smad2 and Smad3.

This data provides the basis for the present invention; according to the present invention, TGFBR1 is now understood to be a gene that, when mutated, causes predisposition to cancer, including pancreatic cancer, colorectal cancer, breast cancer, and NSCLC, or acts as a modifier of other genes resulting in a predisposition. Phenotypes with altered TGFBR1 expression likely accounts for a significant proportion of human cancer, including pancreatic cancer, colorectal cancer, breast cancer, and NSCLC. New mechanistic insights into the role of TGFBR1 signaling in colorectal cancer development both in mixed 129Svlm/C57BL/6 and pure C57BL/6 backgrounds have significant implications for human colorectal cancer. Other data presented herein relate to NSCLC, breast, and pancreatic cancer. The present inventor, based on this evidence, believes that inherited allele-specific expression of TGFBR1 gene acts as a mechanism of predisposition to familial colorectal cancers as well as other cancers such as cancer, including pancreatic cancer, breast cancer, and NSCLC. The differences in expression may be subtle and may include increased, lowered as well as extinguished expression of one allele.

The present inventors also investigated the mechanism by which the reduced dosage effect of TGFBR1 haploinsufficiency may be manifested and found a significant difference in the number of intestinal tumors observed in both mixed 129SvImxC57BL/6 and pure C57BL/6 backgrounds. This provides strong support for the novel concept that decreased TGFBR1-mediated signaling results in the enhanced cell proliferation of normal appearing intestinal epithelial cells within the crypts as well as tumor cells in the presence of preserved TGF-β signaling for cancer, including colorectal cancer, breast cancer, and NSCLC. Survival curves and tumorigenesis for Her2/neu mice that are TGFBR1+/− also suggest decreased TGFBR1-mediated signaling results in a phenotype more susceptible to breast cancer. Haplotypes associated with increased expression of TGFBR1 conferring protection from development of NSCLC in patients show that decreased expression of TGFBR1 is a risk factor for NSCLC.

The present inventor has also discovered that altered phenotypes for TGFBR1 is also important in the development of pancreatic cancer, e.g. constitutively decreased TGFBR1 expression may decrease risk of pancreatic cancer. The fact that decreased expression has been found to correlate with increase of risk in some cancers (NSCLC, colorectal, breast) but the opposite is seen in pancreatic cancer (i.e., risk of pancreatic cancer is decreased upon decreased TGFBR1 expression) illustrates the unexpectedness of the instant invention.

The discovery of the recent invention constitutes the first report of decreased but not abrogated TGF-β signaling resulting in adenocarcinoma formation at 3 months in mice. The discovery of the resent invention constitutes is also the first report of constitutively altered but not abrogated TGF-β signaling upstream of Smad4 associated with increased colorectal tumor development. These results provide strong evidence that constitutively altered Tgfbr1-mediated TGF-β signaling is a potent modifier of colorectal carcinogenesis.

The results with mice bred in a mixed background according to the present invention, is strongly predictive of the relevance of this novel concept in human colorectal carcinogenesis.

Similarly to what was originally observed with the cis-Apc+/Δ716 Smad4+/− mice in which TGF-β signaling is completely abrogated, the same results were found with the F3 (C57BL/6) backcross generation and the fully backcrossed (C57BL/6) generation, except for higher intestinal polyp numbers. It has been previously hypothesized that the reduced polyp numbers in mice with a mixed 129SvImx C57BL6 background is presumably due by the background gene(s) brought in from the 129SvIm strain. Immunohistochemistry analysis show that PCNA levels were inversely correlated with pSmad2 and pSmad3 levels in the intestinal crypts, providing strong support for the notion that increased cellular proliferation is a direct consequence of decreased pSmad2/pSmad3-mediated signaling.

Existing mouse intestinal tumor models based on somatic Apc inactivation display mainly small intestinal lesions, and carcinomas are rare. Inactivation of one copy of the Smad4 gene accelerated tumor progression from intestinal polyps to adenocarcinoma in compound heterozygous cis-Apc+/Δ716 Smad4+/− mice while control cis-Apc+/Δ716 mice developed adenomas but not adenocarcinomas. However, tumor epithelial cells in cis-Apc+/Δ716 Smad4+/− mice carry homozygous mutations in both Apc and Smad4, and there is no evidence of Smad4 protein expression in the colorectal tumor cells. This results in complete abrogation of Smad-mediated TGF-β signaling within intestinal tumors. Similar results have been reported in mice in which the Tgfbr2 allele was knocked out in the intestinal epithelium. In both models, complete abrogation of TGF-β signaling was required to induce malignant transformation of intestinal neoplasms initiated by Apc mutation.

Decreased Tgfbr1 signaling leads to decreased levels of phosphorylated Smad2 and Smad3 in MEFs, in in vitro experiments, and in vivo in the normal appearing colonic epithelium, thus resulting in a global decrease of Smad-mediated signaling. This was observed in vitro upon addition of exogenous TGF-β but was only observed in the intestinal crypts and in patches within tumors in vivo. This highlights the critical role of Tgfbr1 as a potentially limiting factor with respect to the activation of the Smad-signaling cascade at sites of either high TGF-β secretion and/or high cellular proliferation. The absence of effective down regulation of Ccnd1 in Tgfbr1+/− MEFs and the observed increased Ccnd1 levels within the tumors of ApcMin/+; Tgfbr1+/− mice provide the first evidence of the downstream effects of decreased Smad-mediated TGF-β signaling. The TGF-β responses in epithelial cells involve the induction of Cdkn2b by means of the Smads. The decreased Cdkn2b levels observed in Tgfbr1+/− MEFs provide a plausible link between decreased Smad-mediated signaling and increased Ccnd1 expression.

The absence of any obvious phenotype in Tgfbr1+/− mice as well as the absence of phenotypic traits in human beings with constitutionally reduced TGFBR1 expression suggests that decreased Tgfbr1-mediated TGF-β signaling does not affect normal development.

Without being bound by theory, the present invention suggests that decreased Tgfbr1 signaling only becomes a limiting factor when persistently decreased phosphorylation of Smad2 and Smad3 leads to decreased TGF-β signaling, in colorectal cancer, which in turn results in higher cell proliferation. As mutations of the APC gene are among the most commonly encountered genetic hallmarks of human colorectal cancer, altered TGFBR1 signaling is shown by this data as a potent modifier of colorectal cancer development. The impact of decreased Tgfbr1-mediated signaling leading to decreased Smad2 and Smad3 signaling is further highlighted by the recent discovery that both SMAD2 and SMAD3 are among the most commonly mutated genes in human colorectal cancer acting as crucial mediators of colon carcinogenesis.

Thorough histological review of the normal appearing colorectal epithelium and tumor tissues did not reveal difference in the numbers of inflammatory cells in either mouse strain. Together with the findings of comparable lymphocyte counts in ApcMin/+; Tgfbr1+/− and ApcMin/+; Tgfbr1+/+ mice at 12 weeks, this argues against a major role of inflammation as a contributor to the tumor phenotype observed in ApcMin/+; Tgfbr1+/− mice. Nonetheless, TGF-β in tumor infiltrating lymphocytes has been shown to control the growth of dysplastic epithelial cells in experimental colon cancer (Becker et al. "TGF-beta suppresses tumor progression in colon cancer by inhibition of IL-6 transsignaling"). Furthermore, abrogation of TGF-β signaling within T-cells by means of Smad4 inactivation leads to gastrointestinal cancer development (Kim et al. "Smad4 signaling in T cells is required for suppression of gastrointestinal cancer"). These findings suggest that alterations in lymphocyte-mediated TGF-β signaling may contribute to colorectal cancer development in ApcMin/+; Tgfbr1+/− mice through a "landscaping" effect. Additional studies will be needed to clarify the role of decreased Tgfbr1-mediated signaling and assess potential qualitative differences between Tgfbr1+/− and Tgfbr1+/− lymphocytes and stromal cells.

In summary, the discovery of the present invention provides a strong rationale and a plausible mechanism for the novel concept that Tgfbr1 haploinsufficiency has a causative role in cancer, including colorectal cancer, breast cancer, and non-small-cell lung cancer. Tgfbr1 haploinsufficiency is postulated, based on evidence, to have a causative role in breast cancer and NSCLC. However, Tgfbr1 haploinsufficiency, based on evidence, has been found to decrease the risk of pancreatic cancer.

In a broad aspect, therefore, the present invention includes a method for assessing for susceptibility and/or diagnosis of cancer in a patient, comprising determining whether the individual has an allele-specific expression trait in TGFBR1 which results in decreased expression of TGFBR1. Such allele-specific expression can be detected in a variety of ways known in the art, including quantitating expression level of TGFBR1, or by detecting alleles associated with decreased expression of TGFBR1. An alteration in the expression of TGFBR1 (either of message or of protein) compared to a healthy control or an average of healthy controls is indicative of cancer, including pancreatic cancer, breast cancer, and NSCLC, or a predisposition or susceptibility to cancer, including pancreatic cancer, breast cancer, and NSCLC. The alternation of TGFBR1 expression may be either increased expression or decreased expression, relative to healthy controls or a group of healthy controls.

In one embodiment, the present invention includes methods by which to screen TGFBR1 alleles for determination of whether these alleles are associated with decreased expression of TGFBR1, or increased expression of TGFBR1 and detecting for such alleles to detect an individual's predisposition to cancer.

The present invention also includes methods for assessing the genetic predisposition of a subject to develop cancer, including colorectal cancer. At its base, the detection method is based on the differential expression of alleles or presence of their underlying haplotypes of TGFBR1 in normal somatic cells. Differential allelic expression, which can be either increased expression or decreased expression, of TGFBR1 protein is indicative of a higher risk to develop cancer, including pancreatic cancer, breast cancer, and NSCLC. The work of the present inventor leads to the understanding that some TGFBR1 alleles (or their underlying haplotypes) are expressed at lower levels, that this expression level is heritable, and such lowered expression is more common in colorectal cancer patients than normal controls. Thus, either quantitation of expression of TGFBR1 or detection of certain alleles or underlying haplotypes that are associated with differential expression of TGFBR1 may be used to provide information that a subject is more likely to develop cancer, including pancreatic cancer, breast cancer, and NSCLC.

In one embodiment, the present invention includes a method of identifying a candidate compound for modifying TGFBR1 expression, the method comprising: contacting a test compound with a cell expressing TGFBR1; monitoring expression level of TGFBR1; and selecting the test compound as a candidate compound for modifying TGFBR1 expression if the test compound modifies the expression of TGFBR1, relative to the expression of TGRBR1 in a cell of the same cell type that is not contacted with the test compound. Suitable cells include any cell expressing TGFBR1 are known in the art and include cultured cancer cell lines, such as cell lines derived from a tumor such as colorectal tumor, a breast tumor, a non-small cell lung cancer tumor, or a pancreatic tumor. Suitable methods for determining expression level of TGFBR1 in a cell or in a population of cells, including cultured cells, are known in the art. A subset of methods known in the art to quantitate expression levels are described herein. Expression level is modified. In one embodiment, the expression level is decreased. For some cancers, such as, for example, colorectal cancer, breast cancer, and/or NSCLC, a preferred embodiment is a candidate compound that decreases expression of TGFBR1. In another embodiment, the expression level is increased. For some cancers, such as, for example, pancreatic cancer, a preferred embodiment is a candidate compound that increases expression of TFGBR1. The cell may either recombinantly or endogenously express TGFBR1.

The new methods can be used to identify candidate and/or test compounds, e.g., small organic or inorganic molecules (molecular weight less than 1,000 Da), oligopeptides, oligonucleotides, or carbohydrates, that modify expression of TGFBR1. In some embodiments expression is increased. In other embodiments, expression is decreased. In certain embodiments, screens of the present invention utilize libraries of test compounds. As used herein, a "test compound" can be any chemical compound, for example, a macromolecule (e.g., a polypeptide, a protein complex, glycoprotein, or a nucleic acid) or a small molecule (e.g., an amino acid, a nucleotide, an organic or inorganic compound). Examples of test compounds include peptides, peptidomimetics (e.g., peptoids), amino acids, amino acid analogs, polynucleotides, polynucleotide analogs, nucleotides, nucleotide analogs, and organic or inorganic compounds (e.g., heteroorganic or organometallic compounds).

Levels of expression can be measured at the transcriptional and/or translational levels. At the translational level, expression of TGFBR1 can be measured using immunoassays including immunohistochemical staining, western blotting, ELISA and the like with an antibody that selectively binds to TGFBR1 or a fragment thereof. Detection of the protein using protein-specific antibodies in immunoassays is known in the art (see, e.g., Harlow & Lane, Using Antibodies: A Laboratory Manual (1998); Coligan, et al., eds., Current Protocols in Immunology (1991-2006); Goding, Monoclonal Antibodies: Principles and Practice (3rd ed. 1996); and Kohler & Milstein, Nature 256:495-497 (1975). At the transcriptional level, mRNA can be detected by, for example, amplification, e.g., PCR, LCR, or hybridization assays, e.g., northern hybridization, RNAse protection, or dot blotting, all methods known in the art. The level of protein or mRNA is detected, for example, using directly or indirectly labeled detection agents, e.g., fluorescently or radioactively labeled nucleic acids, radioactively or enzymatically labeled antibodies. These assays are well-known to those of skill in the art and described in, e.g., Ausubel, et al., eds., Current Protocols In Molecular Biology (1987-2006).

Modulation (e.g., increase or decrease) of transcriptional levels can also be measured using promoter-reporter gene fusion constructs. For example, the promoter region of a gene encoding TGFBR1 can be fused (i.e., operably linked) to the coding sequence of a polypeptide that produces a detactable signal. Reporter constructs are well known in the art. Exemplary reporter sequences include, for example, fluorescent proteins (e.g., green, red, yellow), phosphorescent proteins (e.g, luciferase), antibiotic resistance proteins (e.g., .beta.-lactamase), enzymes (e.g., alkaline phosphatase).

Selecting the agent that inhibits the activity of the polypeptide. Inhibition of polypeptide activity of TGFBR1 can be measured by comparison to polypeptide activity of the same polypeptide that has not been contacted with one or more candidate agents (inside or outside of a cell). Polypeptide activity that is inhibited will be, e.g., at least about 10%, 25% or 50% less in a treated sample (or reaction mixture) in comparison to an untreated sample. In some embodiments, polypeptide activity can be inhibited at least about 60%, 70%, 80%, 90%, or even completely inhibited, in comparison to polypeptide activity in an untreated sample.

Similarly, inhibition of polypeptide expression of TGFBR1, at the transcriptional or translational level, can be measured by comparison to polypeptide expression levels of the same polypeptide in a cell that has not been contacted with one or more candidate agents. In some embodiments, polypeptide expression levels that are inhibited will be, e.g. at least about 10%, 25% or 50% less in a treated cell in comparison to an untreated cell. In some embodiments, polypeptide expression levels can be inhibited at least about 60%, 70%, 80%, 90%, or even completely inhibited, in comparison to polypeptide expression levels in an untreated cell.

In other embodiments, the inhibition of polypeptide activity or expression in the presence of one or more test agents is compared to polypeptide activity or expression level in the presence of a known inhibitor. In this case, same or similar polypeptide activity or expression levels indicates that the one or more test agents are inhibitors.

In some embodiments, selectivity or specificity of the inhibitory agents can be measured by administering the agent to a cell that does not recombinantly or endogenously express TGFBR1. Agents that specifically inhibit TGFBR1 will generally not elicit any detectable response in a cell that does not express the polypeptide.

In one embodiment, the present invention includes a method to treat or prevent cancer, comprising modifying the expression of TGFBR1. Cancers to treat and/or prevent include pancreatic cancer, NSCLC, colorectal cancer, and/or breast cancer, among others. The methods involve administering to a mammal in need of such treatment a prophylactically or therapeutically effective amount of one or more compounds which alter, or modify, expression of the TGFBR1 gene. Elsewhere herein is discussed the type of compounds which may be candidate compounds for modifying expression. In some embodiments, expression is down-regulated. In some embodiments, expression is up-regulated. Some exemplifications of compounds that are capable of downregulating and/or upregulating expression of TGFBR1 include those described in Uchida H, Kuroki M, Shitama T, Hayashi H, Kuroki M., Activation of TGF-beta1 through up-regulation of TSP-1 by retinoic acid in retinal pigment epithelial cells. Curr Eye Res. 2008 February; 33(2):199-203; Jakowlew S B, Zakowicz H, Moody T W, Retinoic acid down-regulates VPAC(1) receptors and TGF-beta 3 but up-regulates TGF-beta 2 in lung cancer cells, Peptides. 2000 December; 21(12): 1831-7; Yoshizawa M, Miyazaki H, Kojima S., Retinoids potentiate transforming growth factor-beta activity in bovine endothelial cells through up-regulating the expression of transforming growth factor-beta receptors, J Cell Physiol. 1998 September; 176(3):565-73; and A Fadloun, D Kobi, L Delacroix, D Demb|[eacute]|l|[eacute]|, I Michel, A Lardenois, J Tisserand, R Losson, G Mengus & I Davidson Retinoic acid induces TGFbeta-dependent autocrine fibroblast growth, Oncogene 27, 477-489 (17 Jan. 2008).

As discussed hereinabove, one embodiment of the present invention includes measuring allele specific expression (ASE) in a sample of cells from an unaffected subject. The ASE values may then be used to generate a risk score that is predictive of predisposition to cancer, including pancreatic cancer, breast cancer, and NSCLC. ASE may be measured by a variety of techniques that are well known to the art. Quantifying the total or allelic levels of mRNA of TGFBR1 may be used to define the level of total mRNA or the level of ASE. Alternatively, quantifying the levels of the protein product of TGFBR1 may be used to measure expression of TGFBR1. Additional information regarding these methods which are well known in the art may be found in Ausubel et al., (2003) Current Protocols in Molecular Biology, John Wiley & Sons, or Sambrook et al. (1989) Molecular Cloning: A laboratory manual, Cold Spring Harbor Press. A nucleic acid microarray may also be used to quantify the differential expression of TGFBR1. Microarray analysis may be performed using commercially available equipment, using manufacturer's protocols, such as by using the Affy metrix GENECHIP technology or the Microarray System from Incyte (Fremont, Calif.). Typically, single stranded nucleic acids such as cDNAs or oligonucleotides) are plated, or arrayed, on a microchip substrate. The arrayed sequences are then hybridized with specific nucleic acid probes from the cells of interests. Fluorescently labeled cDNA probes may be generated through incorporation of fluorescently labeled deoxynucleotides by reverse transcription of RNA extracted from the cells of interest. Alternatively, the RNA may be amplified by in vitro transcription and labeled with a marker, such as biotin. The labeled probes are then hybridized to the immobilized nucleic acids on the microchip under highly stringent conditions. After stringent washing to remove the non-specifically bound probes, the chip is scanned by confocal laser microscopy or by another detection method, such as a CCD camera. The raw fluorescence intensity data in the hybridization files are generally preprocessed with the robust multichip average (RMA) algorithm to generate expression values.

Quantitative real time PCR (QRT-PCR) may also be used to measure the differential expression of TGFBR1. In QRT-PCR, the RNA template is generally reverse transcribed into cDNA, which is then amplified via a PCR reaction. The amount of PCR product is followed cycle-by-cycle in real time, which allows for determination of the initial concentration of the mRNA. To measure the amount of PCR product, the reaction may be performed in the presence of a fluorescent dye, such as SYBR Green, which binds to double-stranded DNA. The reaction may also be performed with a fluorescent reporter probe that is specific for the DNA being amplified. Multiplex QRT-PCR may be performed by using multiple gene-specific reporter probes, each of which contains a different fluorophore. Fluorescence values are recorded during each cycle and represent the amount of product amplified to that point in the amplification reaction. To minimize errors and sample-to-sample variation, QRT-PCR is typically performed using a reference standard. The ideal reference standard is expressed at a constant level among different tissues, and is unaffected by the experimental treatment. Suitable reference standards include, but are not limited to, mRNAs for the housekeeping genes glyceraldehydes-3-phosphate-dehydrogenase and beta-actin.

Immunohistochemical staining may also be used to measure the differential expression of TGFBR1. The method enables the localization of a protein in the cells of a tissue section by interaction of the protein with a specific antibody. For this, the tissue may be fixed in formaldehyde or another suitable fixative, embedded in wax or plastic, and cut into thin sections using a microtome. Alternatively, the tissue may be frozen and cut into thin sections using a cryostat. The sections of tissue may be arrayed onto and affixed to a solid surface. The sections are then incubated with a primary antibody against the antigen of interest, followed by washed to remove the unbound antibodies. The primary antibody may be coupled to a detection system, or the primary antibody may be detected with a secondary antibody that is coupled to a detection system. The detection system may be a fluorophore or an enzyme, such as horseradish peroxidase, which can convert a substrate into a colorimetric, fluorescent, or chemiluminescent product. The stained tissue sections are generally scanned under a microscope; this measurement, along with a quantification of the intensity of staining, may be used to generate an expression level for TGFBR1. An enzyme-linked immunosorbent assay, or ELISA, may be used to measure the differential expression of the biomarker. There are many variations of an ELISA assay, all are based on the immobilization of an antigen or antibody on a solid surface, generally a microtiter plate. The original ELISA method comprises preparing a sample containing the TGFBR1, coating the wells of a microtiter plate with the sample, incubating each well with a primary antibody that recognizes a specific antigen, washing away the unbound antibody, and then detecting the antibody-antigen complexes. The complexes may be detected directly, where the primary antibody is conjugated to a detection system, or indirectly, where the primary antibody is detected by a secondary antibody that is conjugated to a detection system. The microtiter plate is then scanned and the raw intensity may be converted into expression values using means known in the art.

An antibody microarray may also be used to measure the differential expression of the biomarker. For this, a plurality of antibodies is arrayed and covalently attached to the surface of the microarray or biochip. A protein extract containing the biomarker proteins of interest is labeled with a fluorescent dye. The labeled TGFBR1 proteins are incubated with the antibody array. After washed to remove the unbound proteins, the microarray is scanned, and the raw fluorescence intensity data may be converted into expression values using means known in the art.

Luminex multiplexing microspheres may also be used to measure the differential expression of the biomarker. These microscopic polystyrene beads are internally color coded with fluorescent dyes, such that each bead has a unique spectral signature. Beads with the same signature are tagged with a specific oligonucleotide or specific antibody that will bind the target of interest, e.g., TGFBR1 mRNA or protein). The target, in turn, is also tagged with a fluorescent reporter. There are two sources of color, one from the bead and the other from the reporter molecule on the target. The beads are then incubated with the sample containing the targets. The captured targets are detected by high tech fluidics based on flow cytometry in which lasers excite the internal dyes that identify each bead and also any reporter dye captured during the assay. The data from the acquisition files may be converted into expression values using means known in the art.

In situ hybridization may also be used to measure the differential expression of TGFBR1. This method permits the localization of mRNAs of interest in the cells of a tissue section. Tissue may be frozen, or fixed and embedded, and then cut into thin sections, which are arrayed and affixed onto a solid surface. The tissue sections are incubated with a labeled antisense probe that will hybridize with an mRNA of interest. The hybridization and washing steps are generally performed under highly stringent conditions. The probe may be labeled with a fluorophore or small tag such as biotin, that may be detected by another protein or antibody, such that the labeled hybrid may be detected and visualized under a microscope. Multiple mRNAs may be detected simultaneously, provided each antisense probe has a distinguishable label. The hybridized tissue array is generally scanned under a microscope. Quantification of intensity of staining may be used to generate an expression value for TGFBR1.

In one embodiment, the methods of the instant invention include a method of diagnosis of and/or identification of susceptibility to cancer, including pancreatic cancer, breast cancer, and NSCLC or another cancer in an individual, the method comprising the steps of, in any order: (a) obtaining a sample of the patient's tissue; (b) determining the expression level of TGFBR1; (c) obtaining a reference expression level for TGFBR1 for a normal control; (d) comparing the expression data for TGFBR1 of step (b) with the reference expression for TGFBR1 of step (c), wherein a ratio of the sample expression TGFBR1 to the reference expression of the TGFBR1 indicating altered expression of TGFBR1 in the sample indicates the susceptibility to cancer, including pancreatic cancer, breast cancer, and NSCLC in the individual. An optional step includes generating a report of the susceptibility of the individual to cancer, including pancreatic cancer, breast cancer, and NSCLC. A report may be, without limitation, an oral report, a printed report, or an electronically transmitted report. Altered expression includes decreased expression in one embodiment; in this embodiment, increased susceptibility to colorectal, breast, and/or NSCLC may be diagnosed. In another embodiment, decreased expression indicates decreased susceptibility to pancreatic cancer. By logical extension, increased expression of TGFBR1 may indicate decreased susceptibility and/or risk to colorectal, breast and/or NSCLC cancer; and increased expression of TGFBR1 may indicated increased susceptibility and/or risk of pancreatic cancer.

In one embodiment, the present invention includes a method for the diagnosis and identification of susceptibility to cancer in an individual, comprising: screening a sample from the individual to be diagnosed for at least one allele (or underlying at-risk haplotype) associated with allele specific expression (ASE) in the transforming growth factor beta type 1 receptor gene (TGFBR1) wherein the allele or at-risk haplotype increases the risk significantly. In other embodiments, the cancer includes colorectal cancer, pancreatic cancer, breast cancer, and/or NSCLC.

In one embodiment, the methods of the present invention include a method to detect susceptibility to CRC by identifying haplotypes with lowered expression, in that their presence indicates lowered TGF-beta signaling and therefore higher risk to develop CRC.

Methods of the present invention also include a method of detecting a genetic predisposition in a human subject for developing cancer, including colorectal cancer, pancreatic cancer, breast cancer, and/or NSCLC, comprising the following steps, in any order: a) collecting a biological sample from the subject; b) genotyping the sample at polymorphic nucleotide positions; and c) assessing whether an ASE-associated haplotype is present in the sample, the haplotype comprising polymorphic nucleotide positions wherein the presence of the haplotype indicates a genetic predisposition for developing including colorectal cancer, pancreatic cancer, breast cancer, and/or NSCLC in the subject.

Obtaining a sample of the patient's tissue may be done by any methods known in the art. Bone marrow or lymph node biopsies and analysis of peripheral blood samples for cytogenetic and/or immunologic analysis is standard practice. Frozen tissue specimens may be obtained as well. As used herein a "sample" can be from any organism and can further include, but is not limited to, peripheral blood, plasma, urine, saliva, gastric secretion, feces, bone marrow specimens, primary tumors, metastatic tissue, embedded tissue sections, frozen tissue sections, cell preparations, cytological preparations, exfoliate samples (e.g., sputum), fine needle aspirations, amino cells, fresh tissue, dry tissue, and cultured cells or tissue. It is further contemplated that the biological sample of this invention can also be whole cells or cell organelles (e.g., nuclei). The sample can be unfixed or fixed according to standard protocols widely available in the art.

It is known that the general teaching of measuring gene expression by using PCR based techniques is disclosed in references cited herein, and is well understood by those of skill in the art. Extraction of genomic DNA from peripheral blood or lymphoblastoid cells can be performed by a standard phenol-chloroform procedure; DNA may be extracted from formalin-fixed paraffin-embedded tissue, tumor and normal areas by microdissection, and DNA extracted using a proteinase K and phenol-chloroform method. For total RNA extraction, cells may be processed with TRIZOL reagent and reverse-transcribed using known methods and kits. Polymorphisms in the cDNA can be used as markers to distinguish and measure the expression of alleles, using known methods such as SNAPSHOT (PE Applied Biosystems, Foster City, Calif.). For ASE calculations, the ratio of the two alleles in the cDNA transcript is normalized with the ratio of the two alleles in genomic DNA, applying the following formula: cDNA (peak area common allele/peak area rare allele) divided by gDNA (peak area common allele/peak area rare allele).

Mutation detection may be carried out as known in the art. One example of methods follows. Direct genomic DNA sequencing may be carried out using genomic DNA extracted from blood, and a PCR fragment amplified for each exon, including 50-100 by of each flanking intron. Sequencing may be extended to 2 kb upstream of exon 1 and the entire 3'-UTR region, dividing into overlapping PCR fragments of approximately 500 bp, and products sequenced in both directions using known methods. Another approach includes studying a 96.5 kb genomic region 35 kb upstream of the first exon of TGFBR1 to 12.5 kb downstream of the TGFBR1 3'-UTR. The region can be divided into, for example 18 overlapping amplicons of 1.7 to 10 kb, and each fragment PCR amplified. These long range PCR amplification products can be cloned into chemically competent cells such as TOP10 cells following a standard cloning protocol. Clones may be analyzed by restriction enzyme digestion and forward and reverse sequencing may be performed.

In one step, a biological sample is assessed as to whether an allele specific expression-associated haplotype is present in the sample. As discussed herein, the present inventor had the insight that inherited allele specific expression of the transforming growth factor beta type I receptor gene (TGFBR1) acts as a mechanism for predisposition to familial cancer including colorectal cancer, pancreatic cancer, breast cancer, and/or NSCLC. Without being bound by theory, the present inventor believes that the change to be assessed is subtle; and can be lowered, rather than extinguished, expression of one or more alleles. Population ratio of 1 means that both alleles are equally expressed whereas a ratio of 1.5 means a 33% difference, as does a ratio of 0.67. A cut off point may be selected by using a Receiver Operating Characteristic (ROC) analysis that estimates the sensitivity and specificity of cut off points. In one embodiment, a value of 1.5 is selected to maximize both characteristics providing the highest Youden's index. However, other ratios may be used as well, such as about 1.1, about 1.3, about 1.4, about 1.5, about 1.6, and above about 1.7; any ratio within those named such as, for example, 1.46, may also be used.

A number of methods known in the art in order to select alleles of TGFBR1 by which to screen for allele specific expression and reduced expression, to find candidates to use for screening for haplotypes associated with cancer including colorectal cancer, pancreatic cancer, breast cancer, and/or NSCLC.

For example, it will be a routine matter to compare samples from e.g., cancer patients with putative candidate ASE alleles of TGFBR1 with samples e.g., from patients having wildtype alleles of TGFBR1 to determine the expression ratio to determine whether such candidate alleles result in lower levels of transcription of TGFBR1; those with lowered and/or heightened expression are candidates for alleles associated with predisposition to cancer including colorectal cancer, pancreatic cancer, breast cancer, and/or NSCLC. Statistical and other analysis can be done to validate a candidate allele, once identified with altered or modified expression of TGFBR1, as an allele that leads to predisposition to cancer including colorectal cancer, pancreatic cancer, breast cancer, and/or NSCLC. In one embodiment, patients with ASE values of interest (such as 1.2, or more) may be studied for genetic changes occurring in the germline, including exons, introns, upstream and downstream of 3' UTR, and promoter regions. TGBR1 has nine exons; sequencing may be carried out upstream of exon 1, up to and including 35 kb; and the entire 3' UTR may also be reviewed.

Genotyping of the changes identified by sequencing may then be used to construct haplotypes, using available algorithms such as PHASE v.2.1.1.

Other candidate alleles can comprise alleles of TGFBR1 that are known to be associated with cancer including colorectal cancer, pancreatic cancer, breast cancer, and/or NSCLC. Such alleles include a GCG trinucleotide variable number of tandem repeats which occurs in exon 1 of TGFBR1. The most common allele contains 9 repeats leading to a stretch of 9 alanines in the signal peptide of the receptor protein; the second most common allele has 6 repeats (6A). The 6A allele has been associated with a low level but statistically significant predisposition to several forms of cancer. Such alleles of TGFBR1 known to be associated with cancer can be assessed to determine whether they result in reduced expression of TGFB1. Specific SNPs and ASEs relevant to detection of colorectal cancer include rs334348, rs334349, rs1590, and rs7871490, each of which are described in U.S. Patent Application Ser. No. 61/088,080, filed 12 Aug. 2008, first inventor de la Chappelle et al., "Allele Specific Expression of TGFBR1 Predisposes to Colorectal Cancer," which is hereby incorporated by reference herein in its entirety.

Another allele known to be associated with NSCLC resistance is a 4-SNP CTGC haplotype. See Lei et al., "TGFBR1 Haplotypes and Risk of Non-Small-Cell Lung Cancer", Cancer Res 2009; 69: (17).

The present invention also includes a method of detecting higher than normal risk in a human subject for developing CRC, comprising the steps of, in any order, of: collecting a biological sample from the subject; genotyping the sample at polymorphic nucleotide positions; and assessing whether an ASE-associated haplotype is present in the sample, the haplotype comprising polymorphic nucleotide positions wherein the presence of the haplotype indicates a genetic predisposition for developing cancer including colorectal cancer, pancreatic cancer, breast cancer, and/or NSCLC in the subject.

Methods of the invention also include a method of detecting higher than normal risk in a human subject for developing cancer including colorectal cancer, pancreatic cancer, breast cancer, and/or NSCLC, comprising, in any order: collecting a biological sample from the subject; genotyping the sample at polymorphic nucleotide positions; and assessing whether an ASE-associated haplotype is present in the sample, the haplotype comprising polymorphic nucleotide positions wherein the presence of the haplotype indicates a genetic predisposition for developing cancer including colorectal cancer, pancreatic cancer, breast cancer, and/or NSCLC in the subject.

Methods of the invention also include a method of detecting a predisposition to cancer including colorectal cancer, pancreatic cancer, breast cancer, and/or NSCLC, comprising steps of, in any order, of (1) designing and synthesizing oligonucleotide primers capable of amplifying parts of human TFGBR1 gene and its genomic region, (2) amplifying genomic DNA of cancer including colorectal cancer, pancreatic cancer, breast cancer, and/or NSCLC patients and normal control individuals using the primers of step (1); (3) sequencing the amplified genomic DNA and identifying sequence variations (polymorphisms) of the amplified genomic DNA by comparing it with an existing sequence of human TGFBR1 gene; (4) screening normal control individuals and cancer including colorectal cancer, pancreatic cancer, breast cancer, and/or NSCLC patients for said polymorphisms identified in step (3) by sequencing or genotyping of the amplified genomic DNA of the individuals using the said primers of step (1); (5) computing risk haplotypes for CRC using said polymorphisms in the human TGFRB1 gene and its genomic region based on their frequency distribution in normal individuals and cancer including colorectal cancer, pancreatic cancer, breast cancer, and/or NSCLC patients; and (6) predicting the risk or susceptibility to cancer including colorectal cancer, pancreatic cancer, breast cancer, and/or NSCLC based on the haplotype present at the polymorphic sites in the individuals tested.

In one embodiment, kits are provided for measuring a RNA product of a biomarker of the invention which comprise materials and reagents that are necessary for measuring the expression of the RNA product. For example, a microarray or RT-PCR kit may be used and contain only those reagents and materials necessary for measuring the levels of RNA products. Alternatively, in some embodiments, the kits can comprise materials and reagents that are not limited to those required to measure the levels of RNA products. In a specific embodiment, a microarray or RT-PCR kit contains reagents and materials necessary for measuring the levels of RNA products of TGFBR1, and any number of up to 1, 2, 3, 4, 5, 10 or more genes that are not biomarkers of the invention.

For nucleic acid microarray kits, the kits generally comprise probes attached to a support surface. The probes may be labeled with a detectable label. In a specific embodiment, the probes are specific for the 5' region, the 3' region, the internal coding region, an exon(s), an intron(s), an exon junction(s), or an exon-intron junction(s), of TGFBR1. The microarray kits may comprise instructions for performing the assay and methods for interpreting and analyzing the data resulting from the performance of the assay. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

For RT-PCR kits, the kits generally comprise pre-selected primers specific for particular RNA products (e.g., an exon(s), an intron(s), an exon junction(s), and an exon-intron junction(s)) of TGFBR1. The RT-PCR kits may also comprise enzymes suitable for reverse transcribing and/or amplifying nucleic acids (e.g., polymerases such as Taq), and deoxynucleotides and buffers needed for the reaction mixture for reverse transcription and amplification. The RT-PCR kits may also comprise probes specific for TGFBR1 and/or a specific allele or haplotype or SNP or combination of SNPs of TGFBR1. The probes may or may not be labeled with a detectable label (e.g., a fluorescent label). Each component of the RT-PCR kit is generally in its own suitable container. Thus, these kits generally comprise distinct containers suitable for each individual reagent, enzyme, primer and probe. Further, the RT-PCR kits may comprise instructions for performing the assay and methods for interpreting and analyzing the data resulting from the performance of the assay.

For antibody based kits, the kit can comprise, for example: (1) a first antibody (which may or may not be attached to a support) which binds to protein of interest (e.g., a; and, optionally, (2) a second, different antibody which binds to either the protein, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay.

The term "polynucleotide" is used to mean a polymeric form of nucleotides of any length, which contain deoxyribonucleotides, ribonucleotides, and/or their analogs. The terms "polynucleotide" and "nucleotide" as used herein are used interchangeably. Polynucleotides can have any three-dimensional structure, and can perform any function, known or unknown. The term "polynucleotide" includes double-stranded, single-stranded, and triple-helical molecules. Unless otherwise specified or required, any embodiment of the invention described herein that is a polynucleotide encompasses both the double-stranded form and each of two complementary single-stranded forms known or predicted to make up the double stranded form.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide can be comprised of modified nucleotides, such as methylated nucleotides and nucleotide analogs. Analogs of purines and pyrimidines are known in the art, and include, but are not limited to, aziridinylcytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudouracil, 5 pentynyluracil and 2,6-diaminopurine. The use of uracil as a substitute for thymine in a deoxyribonucleic acid is also considered an analogous form of pyrimidine.

A "fragment" (also called a "region") of a polynucleotide (i.e., a polynucleotide encoding a sarp) is a polynucleotide comprised of at least 9 contiguous nucleotides of the novel genes. Preferred fragments are comprised of a region encoding at least 5 contiguous amino acid residues, more preferably, at least 10 contiguous amino acid residues, and even more preferably at least 15 contiguous amino acid residues.

"Down regulation" or "decreased level of expression" in the context of this invention refers to a sequence corresponding to a gene which is expressed wherein the measure of the quantity of the sequence demonstrates a decreased level of expression of the TGFB1 protein product and/or mRNA compared to "normal" controls. A "decreased level of expression" according to the present invention, is a decrease in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The present invention also includes a method of prevention of colorectal cancer (CRC) morbidity and mortality in a population, comprising administering to individuals in the population a method of detecting a higher than normal risk in a human subject for developing CRC comprising collecting a biological sample from a subject, and/or if an individual has at least one risk factor selected from the group consisting of: an at-risk haplotype for CRC, an at-risk haplotype in the TGFBR1 gene; an at-risk polymorphism in TGFBR1; dysregulation of TGFBR1 mRNA expression, dysregulation of a TGFBR1 mRNA isoform; for decreased TGFBR1 protein expression, said individual can then undergo cancer testing, such as routine colonoscopy, and potentially therapy to prevent CRC from developing or spreading, thereby lowering CRC morbidity and mortality.

EXAMPLES

Example 1

Generation of a Targeted Tgfbr1 Mouse Model

Using mouse genomic DNA as a template, Tgfbr1 primers were designed amplifying a 491 base pair fragment spanning from position 27 (exon 1) to position 517 (exon 3). Using an isogenic 129SvIm genomic library (Stratagene), several clones were chosen, grown, and the insert was excised through NotI cleavage. Two overlapping clones were obtained that spanned this genomic region. A NotI site 5-bp was found downstream of the ATG start codon. The targeting vector has been designed to insert the Neo cassette into the Not I site, thus interrupting the Tgfbr1 open reading frame and removing 1.1 kb mouse genomic sequence immediately upstream of this Not I site.

Referring to FIG. 1, generation of a novel Tgfbr1 exon knockout mouse model is seen. In FIG. 1A, a strategy for interrupting the Tgfbr1 open reading frame by insertion of a Neo cassette is seen. A classical targeting vector inserting was generated by inserting a Neomycin resistance cassette (Neo) into a Not I site located immediately after the start codon and removing 1.1 kb of mouse genomic sequence immediately upstream of this Not I site.

Following transfection and selection of 129SvIm embryonic stem (ES) cells, KO clones were karyotyped and injected into C57BL/6 blastocysts. Germline transmission from the resulting chimeras was obtained and a colony established. F3 Tgfbr1+/− mice were backcrossed into the C57BL6/J background using speed congenics markers. Briefly, a minimum of 8 Tgfbr1+/− animals from each generation of backcrossing were genotyped for 152 markers by the Jackson Laboratory (Bar Harbor, Me.). Mice with the highest percentage of the host genome were used to backcross to the host for the next generation. Two fully congenic F6 males (99.9% C57BL6/J) were confirmed using a full genome wide panel of 150 SNP markers (Jackson laboratory, Bar Harbor, Me.). These two males were crossed with C57BL6/J females to obtain pure Tgfbr1+/− mice in the C57BL6/J background.

Tgfbr1+/− genotype was confirmed by PCR analysis using the following set of 3 primers: 5'-AGACCCCAGCTCT-TAGCCCCCA-3'(SEQ ID NO:1), 5'-GAGACGCTCCAC-CCACCTTCCC-3' (SEQ ID NO:2), and 5'-GAAGCT-GACTCTAGAGGATCCC-3'(SEQ ID NO:3). PCR amplification results in 2 bands in Tgfbr1+/− mice (240 bp and 314 bp, corresponding to the knocked-out and WT Tgfbr1 allele, respectively). Referring to FIG. 1B, PCR genotyping for the Tgfbr1+/− allele using 3 primers reveals a 2nd band at 240 bp, corresponding to the knocked out allele, and the wild type Tgfbr1 band at 314 bp is seen. Pure Tgfbr1+/− female mice in C57BL6/J were mated with C57BL/6J ApcMin/+ male mice to generate pure C57BL6/J animals harboring Tgfbr1+/− or Tgfbr1+/+. The ApcMin/+ locus was detected by PCR using the following primers: 5'-TTCCACTTTG-GCATAAGGC-3'(SEQ ID NO:4), 5'-TTCTGAGAAAGA-CAGAAGTTA-3' (SEQ ID NO:5). PCR amplification results in a band of 340 bp. There was no evidence of expression of the neomycin cassette in the germline of Tgfbr1+/− mice.

Histopathology of Intestinal Polyps and Polyp Scoring.

The number and size of polyps were scored by two examiners. Tissue specimens were prepared according to standard protocols. Polyps from seven randomized mice from each group were sectioned, stained with H&E, to differentiate tumors from lymphoid aggregates.

Mouse Embryonic Fibroblasts.

Mouse embryonic fibroblasts (MEFs) were collected at embryonic day 12.5 according to standard protocol (Hogan B, Beddington R, Costantini F, Lacy E. "Manipulating the mouse embryo". 2nd ed. Cold Spring Harbor Laboratory Press; 1994) and cultured in DMEM (Invitrogen, Carlsbad, Calif.) supplemented with 10% FBS (Hyclone, Logan, Utah), 2 mM L-glutamine, and 100 units/ml penicillin/streptomycin (Tsutsui T, Hesabi B, Moons D S, Pandolfi P P, Hansel K S, Koff A, et al. "Targeted disruption of CDK4 delays cell cycle entry with enhanced p27(Kip1) activity". Molecular & Cellular Biology 1999 October; 19(10): 7011-9).

Spontaneous Cell Proliferation Assays.

MEFs were seeded in normal growth medium at a concentration of $5 \times 10^4$ cells per well in 6 well plates on day 0. Cell number was determined by trypsinizing and counting cells on day 1, 2 and 3.

TGF-β-mediated Cell Proliferation Assays.

TGF-β-mediated cell growth inhibition was assessed by 3Hthymidine incorporation assays (Pasche B, Knobloch T J, Bian Y, Liu J, Phukan S, Rosman D, et al. "Somatic Acquisition and Signaling of TGFBR1*6A in Cancer". JAMA: The Journal of the American Medical Association 2005 Oct. 5; 294(13):1634-46).

Luciferase Assays.

The 3TP-Lux and SBE4-Lux reporter constructs were gifts of Dr. Joan Massagué (Sloan-Kettering) and Dr. Bert Vogelstein (Hopkins). The experiments were performed as described before (Rosman D S, Phukan S, Huang C C, Pasche B. "TGFBR1*6A Enhances the Migration and Invasion of MCF-7 Breast Cancer Cells through RhoA Activation". Cancer Res 2008 Mar. 1; 68(5):1319-28).

Immunoblotting and Immunohistochemistry.

Nuclear extracts from mouse embryonic fibroblast were obtained using a NE-PER nuclear and cytoplasmic extraction kit (Thermo Fisher Scientific, Inc., Rockford, Ill., cat #78833). Cell lysates were collected in lysis buffer (TNT buffer (10 mM Tris pH 8.0, 1% Triton X-100, 1 mM EDTA, 150 mM NaCl), supplemented with Phosphatase Inhibitor Cocktails 1 and 2, and Protease Inhibitor Cocktail (Sigma, St. Louis, Mo.)), and centrifuged at 14000×g for 15 min. above. All lysates were separated by SDS-PAGE gels (Invitrogen, Carlsbad, Calif.), and transferred onto nitrocellulose (GE Healthcare, Buckinghamshire, England). Immunoblotting was done using the following antibodies: rabbit anti-TG-FBR1 (sc-398), anti-cyclin D1 (sc-753), anti-TGFBR2 (sc-220), antip15 (sc-613), anti-Cdk4 (sc-260), mouse anti-Cdk2 (sc-6248), anti-Cdk6 (sc-56282), anti-p21 (sc-6246), anti-p27 (sc-1641), and anti-Histone 1 (sc-8030) (Santa Cruz Biotechnology, Santa Cruz, Calif.); rabbit anti-pSmad2 (cat #3101) (Cell Signaling Technology, Boston, Mass.); rabbit anti-pSmad3 was a gift from Dr. Koichi Matsuzaki, Kanzai Medical University, Osaka, Japan. Signal detection was measured by SuperSignal West Femto Chemiluminescent Substrate (Thermo Fisher Scientific, Inc., Rockford, Ill.). Films were scanned and densitometry was performed using Fujifilm LAS-3000 (Fuji Medical System, USA). Immunohistochemistry was performed with the Dako EnVision System (Carpinteria, Calif.). Percentage of positively stained cells was determined by assessing the number of strongly positive stained cells out of the total number of cells in a field. Five representative fields in 3 different samples were assessed.

Loss of Heterozygosity (LOH) Analyses.

SNaPshot methodology (PE Applied Biosystems, Foster City, Calif.) was used to identify each allele, and to detect loss of heterozygosity (LOH) in tumor DNA.

Statistical Analysis.

Data were analyzed by Student's t-test and are expressed as mean±S.E.M. p values<0.05 were considered significant. All tests were two-tailed. Data were transformed in logarithm scale when normality assumption was violated. One-way ANOVA was used for the analysis of Tgfbr1 expression in various tissues. Referring to FIG. 1C, Quantitative RT-PCR assessment of Tgfbr1 expression levels in mouse embryonic fibroblasts (M), colon intestinal tissue (C), tail (T), and peripheral lymphocytes (L) of Tgfbr1+/+ and Tgfbr1+/− mice is seen. Tissues were collected from three animals of each genotype. Each experiment was performed at least three times in triplicates. Tgfbr1 levels in Tgfbr1+/− tissues are expressed as ratio of Tgfbr1/Gapdh compared to each corresponding Tgfbr1+/+ tissue. Chi-square analysis was used to compare the proportion of intestinal tumors in Tgfbr1+/− and Tgfbr1+/+ mice and the proportion of colonic tumors in Apc-Min/+; Tgfbr1+/− and ApcMin/+; Tgfbr1+/+ mice.

Example 2

Generation of a Novel Mouse Model of Targeted Tgfbr1 Inactivation

A knockout mouse model of TGFBR1 generated by targeted deletion of exon 3 has been previously described. There is growing evidence that the signal sequence of human TGFBR1*6A may have intrinsic biological effects, which are caused by mutations within the exon 1 GCG repeat sequence. While the exon 3 Tgfbr1 knockout model does not result in the generation of functional TGFBR1, the generation of a functionally active signal sequence cannot be excluded. To circumvent this potential problem, a classical knockout vector was designed to insert a Neomycin resistance cassette (Neo) into a Not I site located immediately after the start codon and removing 1.1 kb of mouse genomic sequence immediately upstream of this Not I site (FIG. 1A). This approach precludes the generation of any signal sequence, which is encoded by part of the removed sequence. The Tgfbr1+/− mice were viable and fertile, and appeared normal in their morphology and behavior. A total of 50 pups from the heterozygous intercrosses were genotyped, and no Tgfbr1−/− pups were found, with only the wild-types and the heterozygotes at the ratio of 1:2. Dead Tgfbr1−/− embryos were found at a ratio of 1:4 at the time of collection of MEFs. These findings are consistent with the previous report of targeted disruption of Tgfbr1 exon 3 in which mice lacking Tgfbr1 die at midgestation. Therefore, the stage of lethality was not determined. At 16-months, follow-up of 10 Tgfbr1+/− mice does not suggest increased mortality as compared with 10 wild-type littermates.

Tgfbr1 expression levels in different tissues were first compared by real-time PCR. Tgfbr1 expression in Tgfbr1+/− tissues ranged from 54% in embryonic fibroblasts to 62% in colonic epithelium, 44% in tail and 67% in blood lymphocytes when compared with corresponding expression levels in Tgfbr1+/+ mice (FIG. 1C). Tissue-specific differences between Tgfbr1+/− and Tgfbr1+/+ mice were significant for each corresponding tissue, p=0.016 for embryonic fibroblasts, p=0.04 for colonic epithelium, p=0.009 for tail, and p=0.01 for blood lymphocytes. The differences in Tgfbr1 expression levels between the various Tgfbr1+/− tissues were not statistically significant, p=0.429. To assess the functional consequences of Tgfbr1 haploinsufficiency we measured Tgfbr1 and Tgfbr2 protein expression in MEFs. Tgfbr1 expression levels were lower in the Tgfbr1+/− MEFs than in Tgfbr1+/+ MEFs.

Referring to FIG. 1D, Western blot analysis of Tgfbr1 and Tgfbr2 expression of two representative pairs of MEFs from Tgfbr1+/+ and Tgfbr1+/− mice is seen. As expected, Tgfbr2 levels were similar.

Tgfbr1 Haploinsufficiency Enhances Tumor Formation.

Figure 2:
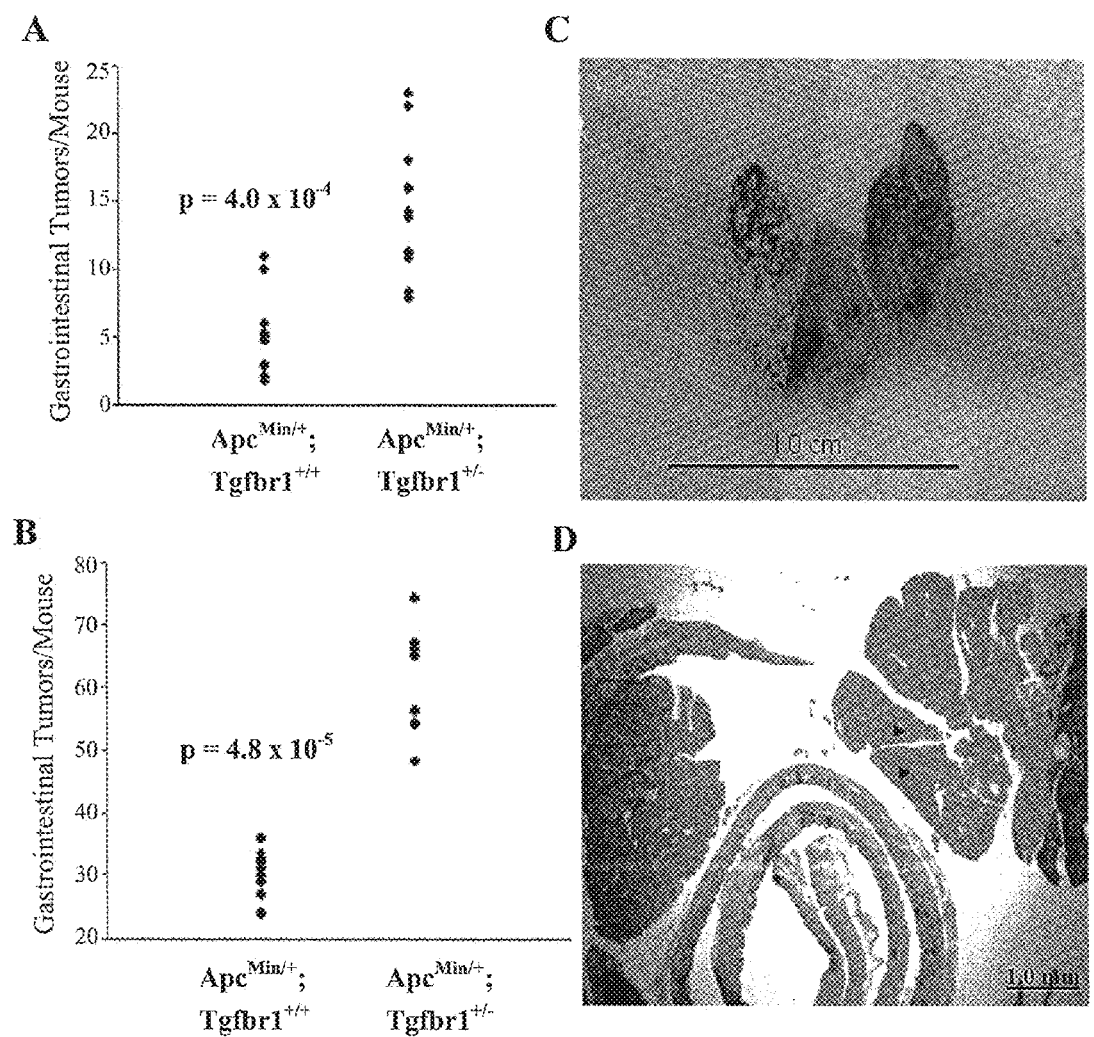
FIGS. 2A-2D show Tumorigenesis of ApcMin/+; Tgfbr1+/+ and ApcMin/+; Tgfbr1+/− mice.

Because the gastrointestinal tract is a common site of cancer in humans with constitutively altered TGF-β signaling, the effect of Tgfbr1 haploinsufficiency on ApcMin/+-mediated intestinal tumorigenesis was tested. ApcMin/+ mice harbor a premature stop codon in one allele of the Apc tumor suppressor gene (ApcMin/+). These mice develop multiple intestinal adenomas and mimic human familial adenomatosis polyposis coli. Tgfbr1+/− female mice on the 129/SvIm background were backcrossed into the C57BL/6 background. F2 Tgfbr1+/− females were crossed with ApcMin/+ male mice (C57BL/6). Mice were sacrificed at 12 weeks and examined for intestinal tumors. The tumors counted were verified by histology. No tumors were observed in the small and large bowels of 8 Tgfbr1+/+ and 9 Tgfbr1+/− mice in wild type Apc background. A total of 9 ApcMin/+; Tgfbr1+/+ mice developed an average of 5.4±1.7 tumors (mean±S.E.M.) while the number of tumors observed in 10 ApcMin/+; Tgfbr1+/− mice was almost three times higher: 14.5±1.1 tumors. Referring to FIG. 2, tumorigenesis of ApcMin/+; Tgfbr1+/+ and ApcMin/+; Tgfbr1+/− mice is seen. In FIGS. 2A and B, number of gastrointestinal tumors per mouse at 12 weeks of age for ApcMin/+; Tgfbr1+/+ mice (n=9) and ApcMin/+; Tgfbr1+/− littermates (n=10) in mixed 129SvIm/C57BL/6 background (FIG. 2A) and ApcMin/+; Tgfbr1+/+ mice (n=12) and ApcMin/1+; Tgfbr1+/− littermates (n=7) in C57BL/6 background (FIG. 2B) is seen. The data represents mean±S.E.M. The difference in the number of tumors between the two groups was highly significant: 9.8 tumors (95% CI, 4.8-13.4), p=0.0004. The majority of tumors was small (less than 3 mm) and predominantly scattered in the small intestine. Five ApcMin/+; Tgfbr1+/− mice (50%) had an average of 2.4±0.2 colonic tumors while only two ApcMin/+; Tgfbr1+/+ mice (22%) had one colonic tumor each, a non-significant difference, p=0.437. The identity of each lesion as tumor rather than lymphoid aggregates was confirmed in seven mice from each group by histopathology.

To determine the reproducibility of our initial findings obtained in a mixed 129SvIm×C57BL/6 background, we repeated these experiments with Tgfbr1+/− mice, which were fully backcrossed into the C57BL/6 using speed congenics markers. As seen in FIG. 2B, there was an average of 30.2±0.9 tumors in 12 ApcMin/+; Tgfbr1+/+ mice and 61.4±3.4 tumors in 7 ApcMin/+; Tgfbr1+/− mice (mean±S.E.M.). The difference in the number of tumors between the two groups was highly significant: 31.2 tumors (95% CI, 25.3-37.2), p=4.8×10-5. Importantly, the number of colonic tumors was higher among ApcMin/+; Tgfbr1+/− mice (4.9±0.3) than among ApcMin/+; Tgfbr1+/+ mice (3.0±0.4), p=0.0005. Six ApcMin/+; Tgfbr1+/− mice (three in the mixed background and three in the pure C57BL/6 background) exhibited large colonic tumors with a maximal diameter greater than 7 mm Referring to FIG. 2C, large polyps arising from ApcMin/+; Tgfbr1+/− mouse colonic mucosa at 12 weeks is seen, scale bar, 1 cm.

Referring to FIG. 2D, histological analysis of the large polypoid colonic tumor from the ApcMin/+; Tgfbr1+/− mouse shown in FIG. 2C is seen. Black arrowheads represent presence of carcinoma, scale bar, 1 mm. Scale bar, 100 μM. Histological analysis of these polypoid and ulcerated colonic tumors revealed the presence of carcinoma (FIG. 2D) as evidenced by the presence of distinct cytological and nuclear atypia. The largest tumors in the ApcMin/+; Tgfbr1+/+ mice in either the mixed 129SvIm/C57BL/6 or the pure C57BL/6 backgrounds were 3 mm in size and none of them harbored carcinoma. Among all mice examined at 12 weeks the proportion of ApcMin/+; Tgfbr1+/− mice with colonic tumors greater than 7 mm (35.3%) harboring carcinoma was significantly higher than that of ApcMin/+; Tgfbr1+/+ mice (0%), p=0.018.

Example 3

Figure 3:
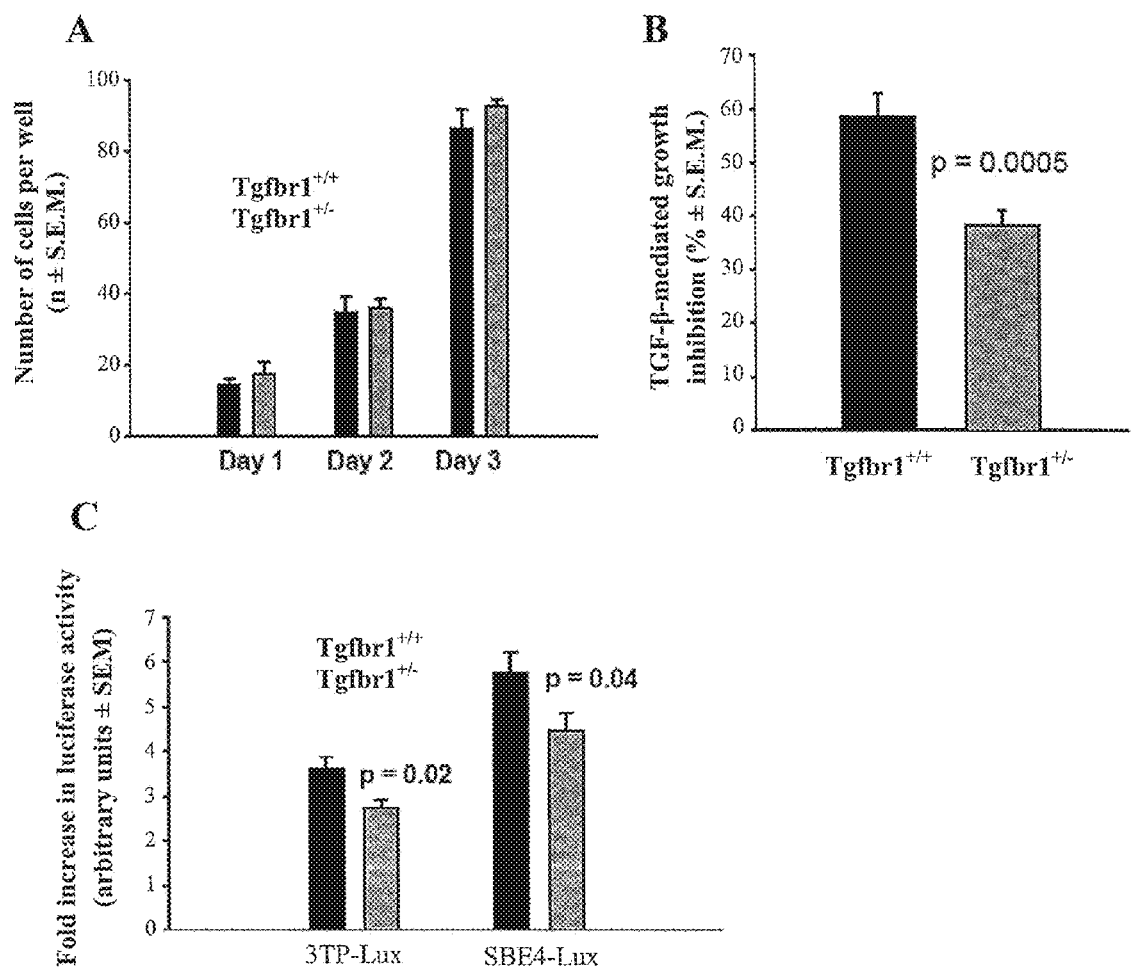
FIGS. 3A-3C show TGF-β-mediated cell proliferation of Tgfbr1+/+ and Tgfbr1+/− mouse embryonic fibroblasts (MEFs).

Tgfbr1 Haploinsufficiency Modifies TGF-β-mediated Signaling and Cell Proliferation but does not Alter Hematopoiesis Next the effects of Tgfbr1 haploinsufficiency on cell proliferation were studied using mouse embryonic fibroblasts (MEFs) from Tgfbr1+/+ and Tgfbr1+/− mice. In the absence of TGF-β, the growth of Tgfbr1+/+ and Tgfbr1+/− MEFs was identical. Referring to FIG. 3, TGF-β-mediated cell proliferation of Tgfbr1+/+ and Tgfbr1+/− mouse embryonic fibroblasts (MEFs) is seen. FIG. 3A shows spontaneous cell proliferation of Tgfbr1+/+ and Tgfbr1+/− MEFs. Cell proliferation was assessed daily for three days by counting cells. The experiments were performed three times in triplicates. The data show mean cell count±S.E.M. In the presence of exogenously added TGF-β, the proliferation of Tgfbr1+/− MEFs decreased by 38.32±3.44% while that of Tgfbr1+/+ MEFs decreased by 58.24±5.74%, p=0.0005. FIG. 3B shows TGF-β-mediated cell proliferation assays. TGF-β-mediated cell proliferation was assessed in Tgfbr1+/− and Tgfbr1+/+ MEFs exposed to 100 pM TGF-β1 for 24 hours. Cell proliferation was assessed by thymidine incorporation. The experiments were performed three times in triplicates. The data show mean TGF-β growth inhibition in %±S.E.M. To directly analyze the signaling activity of Tgfbr1+/+ and Tgfbr1+/− MEFs, the TGF-β reporter 3TP-lux (26) and the TGF-β reporter SBE4-Lux we reused as readouts. Referring to FIG. 3C, direct measurement of TGF-β signaling using the 3TP-Lux and SBE4-Lux reporter assays in Tgfbr1+/+ and Tgfbr1+/− MEFs following exposure to 100 pM TGF-β is seen. Data represent the average of three experiments performed in triplicates. The data show fold increase in arbitrary units±S.E.M. As seen in FIG. 3C, following addition of TGF-β3 to the cell culture medium, induction of TGF-β signaling was significantly higher for Tgfbr1+/+ than Tgfbr1+/− MEFs for 3TP-Lux (3.62 fold vs. 2.73 fold) (p=0.02) and SBE4-Lux (5.76 fold vs. 4.47 fold) (p=0.04). The differences between Tgfbr1+/+ and Tgfbr1+/− with respect to the induction of SBE4-Lux and 3TP-Lux upon exposure to TGF-β were almost similar, 24.6% and 22.4%, respectively.

Because the TGF-β signaling pathway is a potent regulator of hematopoietic differentiation and because alterations in lymphocyte TGF-β signaling have been implicated in colorectal tumor progression in mice, whether Tgfbr1 haploinsufficiency had any measurable effects on the hematopoietic compartment was determined. Complete blood counts of five Tgfbr1+/− and five Tgfbr1+/+ mice obtained at 12 weeks did not reveal any difference in the average red blood cell, white blood cell or platelet numbers, thus indicating that Tgfbr1 haploinsufficiency alone does not significantly alter hematopoiesis. The average lymphocyte count was 13.11±0.31 and 12.73±0.55 (mean±S.D.) for Tgfbr1+/− and Tgfbr1+/+ mice, respectively, a non-significant difference, p=0.181.

Example 4

Tgfbr1 Haploinsufficiency Impairs Smad2 and Smad3 Signaling

Figure 4:
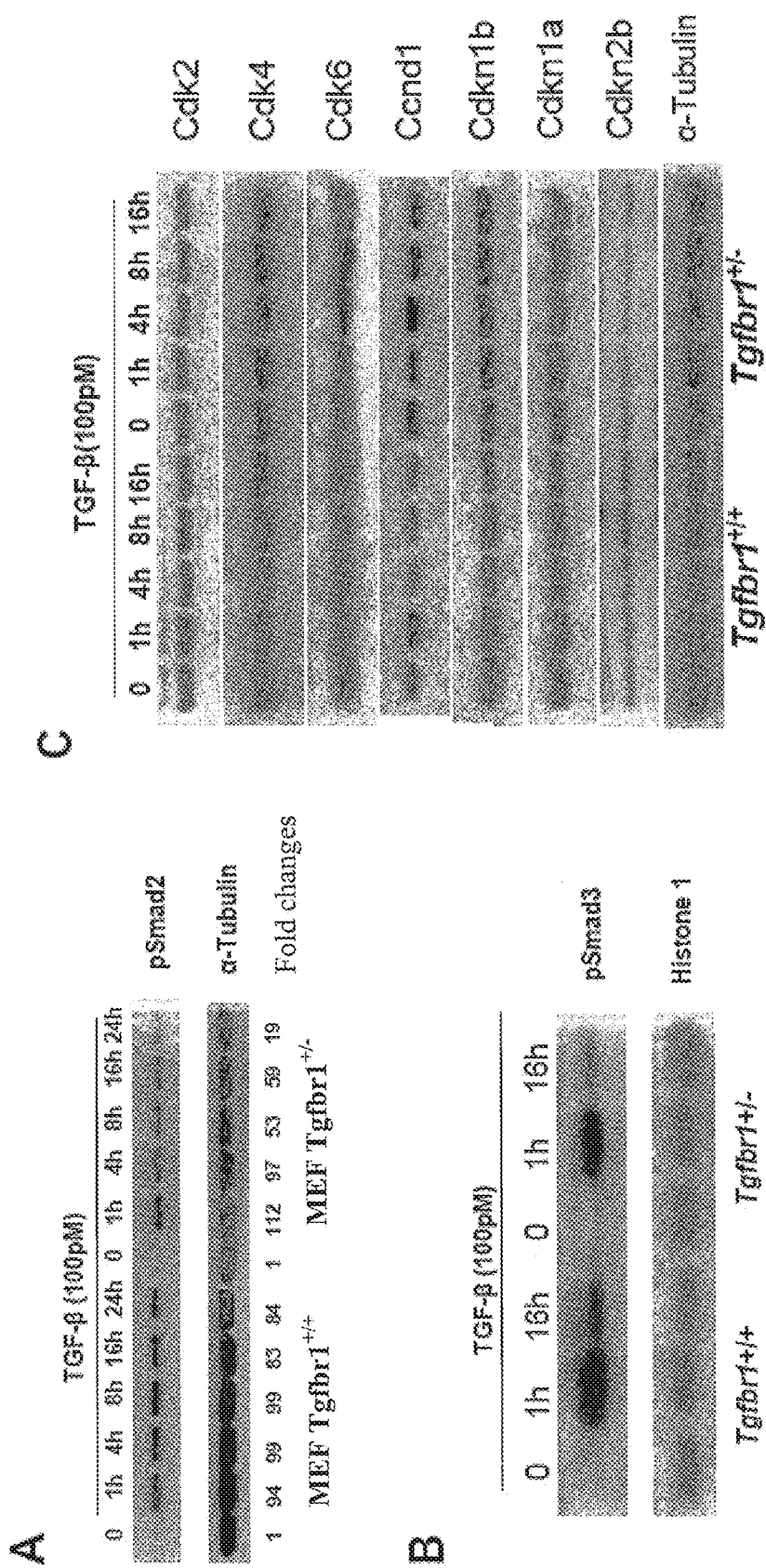
FIGS. 4A-4C show TGF-β-mediated Smad signaling of Tgfbr1+/+ and Tgfbr1+/− mouse embryonic fibroblasts (MEFs).

The levels of TGF-β-mediated generation of pSmad2 in Tgfbr1+/+ and Tgfbr1+/− MEFs were first assessed over 24 hours. While pSmad2 levels were almost identical at 1 and 4 hr, pSmad2 levels decreased by approximately 50% at 8 hr and 80% at 24 hr in Tgfbr1+/− MEFs while they decreased only slightly in Tgfbr1+/+ MEFs. Referring to FIG. 4, TGF-β-mediated Smad signaling of Tgfbr1+/+ and Tgfbr1+/− mouse embryonic fibroblasts (MEFs) is seen. FIG. 4A shows assessment of pSmad2. Levels of phosphorylated Smad2 (pSmad2) following exposure of MEFs to TGF-β1 were assessed in three pairs of Tgfbr1+/+ and Tgfbr1+/− MEFs from six different mice. The MEF pair presented is representative of the three pairs of MEFs. It has been previously shown that phosphorylation of Smad3 is an essential step in signal transduction by TGF-β for inhibition of cell proliferation and Smad3-deficient mice are prone to colon cancer development. To assess the impact of Tgfbr1 haploinsufficiency on the phosphorylation of Smad3 an antibody targeting the Ser423/425 site on Smad3 (32;33) was used. FIG. 4B shows an assessment of pSmad3. Levels of phosphorylated Smad3 (pSmad3) following exposure of MEFs to TGF-β1 in three pairs of Tgfbr1+/+ and Tgfbr1+/− MEFs. MEF nuclear extracts were used for Western blot analysis probed with pSmad3 antibodies. Histone 1 is a loading control for nuclear protein extracts. The MEF pair presented is representative of the three pairs of MEFs. As seen in FIG. 4B, following exposure to TGF-β pSmad3 levels were higher at 1 and 16 h in Tgfbr1+/+ MEFs than in Tgfbr1+/− MEFs. Hence, Tgfbr1 haploinsufficiency was associated with a small but significant decrease in TGF-β signaling mediated by decreased phosphorylation of both Smad2 and Smad3.

Example 5

Downstream Effects of Decreased Tgfbr1-mediated Signaling In Vitro

To dissect the downstream effects of decreased TGF-β signaling we assessed the expression levels of selected mediators of the cell cycle and downstream effectors of TGF-β signaling. FIG. 4C shows differential regulation of cell cycle mediators: Western blot analysis of Tgfbr1+/+ and Tgfbr1+/− MEFs in the absence (time 0) and in the presence of 100 pM TGF-β1 for 1, 4, 8, and 16 h. The MEF pair presented is representative of the three pairs of MEFs. As seen on FIG. 4C, there was no difference in the levels of these mediators in the absence of TGF-β with the exception of mildly decreased baseline levels of Ccnd1 in Tgfbr1+/+ MEFs when compared with Tgfbr1+/− MEFs. This differential expression pattern was markedly enhanced following exposure to TGF-β as exemplified by reduced Ccnd1 expression in Tgfbr1+/+ MEFs after 4 hours while Ccnd1 levels initially increased and remained elevated at 16 hours in Tgfbr1+/− MEFs (FIG. 4C). Levels of Cdkn2b remained unchanged upon exposure to TGF-β in Tgfbr1+/+ MEFs while a small decrease was observed in Cdkn2b levels in Tgfbr1+/− MEFs. The emergence of differential expression of pSmad2 (FIG. 4A), pSmad3 (FIG. 4B), and Ccnd1 (FIG. 4C) levels occurred in parallel, which suggests that decreased Smad signaling results in persistently high Ccnd1 levels in Tgfbr1+/− MEFs.

Example 6

Figure 5:
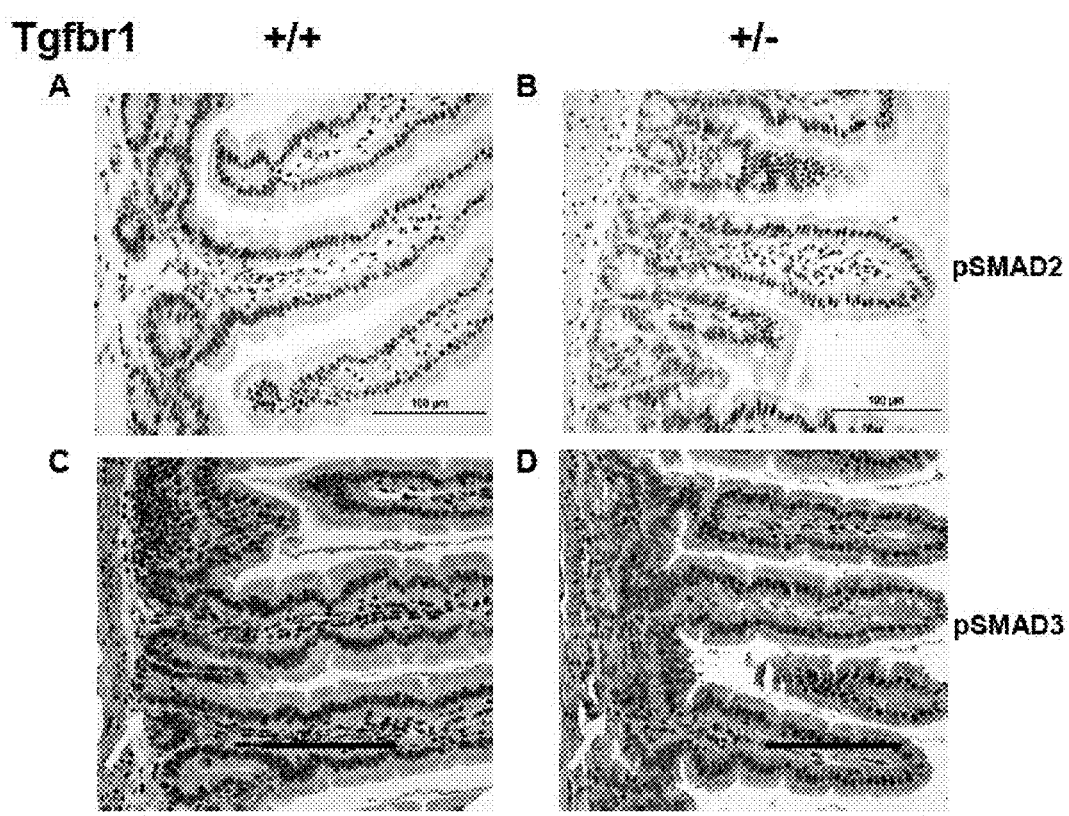
FIGS. 5A-5D show immunohistochemistry staining patterns of normal appearing small bowel tissues from ApcMin/+; Tgfbr1+/+ and ApcMin/+; Tgfbr1+/− mice.

Characterization of Tgfbr1 Haploinsufficiency Effects on the Intestinal Epithelium To characterize the in vivo consequences of constitutively decreased TGF-β signaling, pSmad2 immunostaining of normal appearing intestinal tissue and tumor sections was performed. Referring to FIG. 5, immunohistochemistry staining patterns of normal appearing small bowel tissues from ApcMin/+; Tgfbr1+/+ and ApcMin/+; Tgfbr1+/− mice is seen. Normal appearing small intestine stained with pSmad2 shows identical staining pattern throughout the villi of both ApcMin/+; Tgfbr1+/+ mice (FIG. 5A) and ApcMin/+; Tgfbr1+/− mice (FIG. 5B); however, pSmad2 staining within the intestinal crypts of ApcMin/+; gfbr1+/− mice (arrow) is reduced when compared with that of their wild type counterparts (arrow). While pSmad2 staining was homogeneous throughout the intestinal mucosa of ApcMin/+; Tgfbr1+/+ mice (FIG. 5A), reduced pSmad2 staining was observed in the crypts but not in the villi of ApcMin/+; Tgfbr1+/− mice (FIG. 5B). To comprehensively assess the impact of Tgfbr1 haploinsufficiency on Smad-mediated TGF-β signaling pSmad3 immunostaining of the same tissues was performed. Referring again to FIG. 5, normal appearing small intestine stained with pSmad3 shows identical staining pattern throughout the villi of both ApcMin/+; Tgfbr1+/+ mice (FIG. 5C) and ApcMin/+; Tgfbr1+/− mice (FIG. 5D); however, pSmad3 staining within the intestinal crypts of ApcMin/+; Tgfbr1+/− mice (arrow) is reduced when compared with that of their wild type counterparts (arrow). As seen in FIG. 5C, homogeneous pSmad3 staining was observed in the crypts of ApcMin/+; Tgfbr1+/+ mice while pSmad3 staining was markedly reduced in the crypts of ApcMin/+; Tgfbr1+/− mice (FIG. 5D), mirroring the pSmad2 findings and demonstrating that Tgfbr1 haploinsufficiency results in decreased phosphorylation of both receptor Smads within the intestinal epithelial crypts thus resulting in overall decreased Smad-mediated TGF-β signaling in vivo. To determine whether the differential expression of Smads within the intestinal crypts modifies cellular proliferation in vivo, the levels of proliferating cell nuclear antigen (PCNA) in the normal intestinal epithelium of ApcMin/+; Tgfbr1+/+ and ApcMin/+; Tgfbr1+/− mice were assessed. PCNA staining was significantly more intense in ApcMin/+; Tgfbr1+/− mice (62.2±2.2% positive staining) than in their wild type counterpart (44.4±2.8% positive staining) (p=0.008), thus confirming in vivo the observed in vitro increased cellular proliferation of Tgfbr1+/− upon exposure to TGF-β.

Example 7

Characterization of Tgfbr1 Haploinsufficiency Effects on Intestinal Tumors

Figure 6:
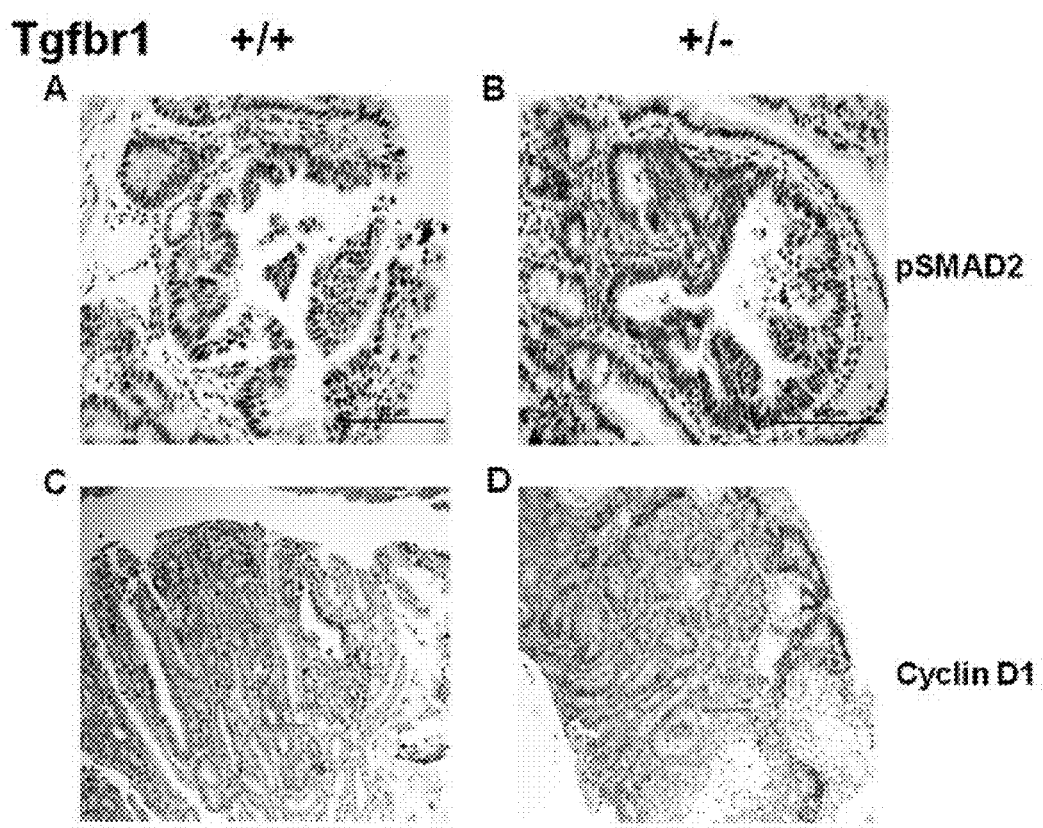
FIGS. 6A-6D show characterization of Tgfbr1 haploinsufficiency on molecular signaling within tumors.

Tumors arising from both ApcMin/+; Tgfbr1+/+ and Apc-Min/+; Tgfbr1+1-mice had uniform pSmad staining reflecting preserved in vivo Smad signaling. Referring to FIG. 6, characterization of Tgfbr1 haploinsufficiency on molecular signaling within tumors is seen. pSmad2 staining is patchy within tumors arising from ApcMin/+; Tgfbr1+/− mice, which reflects focally-decreased Smad-mediated TGF-β signaling (FIG. 6B), whereas tumors arising from ApcMin/+; Tgfbr1+/+ mice have uniform pSmad2 staining showing preserved Smad-mediated TGF-β signaling (FIG. 6A). However, focal areas of decreased pSmad2 staining was found among ApcMin/+; Tgfbr1+/− mice tumors (FIG. 6B) but not in their wild type counterparts (FIG. 6A). Consistent with the findings of preserved TGF-β signaling activity in the tumors of both ApcMin/+; Tgfbr1+/+ and ApcMin/+; Tgfbr1+/− mice, no evidence of Tgfbr1 loss of heterozygosity was found in six microdissected colonic tumors from three different Apc-Min/+; Tgfbr1+/− mice. The combined evidence from pSmad2 IHC as well as LOH analysis of intestinal tumors demonstrate that reduced dosage rather than abrogation of Tgfbr1-mediated Smad signaling is sufficient to enhance the Apc-mediated development of intestinal tumors and adenocarcinoma at 12 weeks.

The role of Ccnd1 as a mediator of colon cancer development and progression is reflected by the fact that decreased Ccnd1 expression reduces tumor formation in ApcMin/+ mice. Conversely, the role of the Wnt pathway in promoting intestinal stem cell proliferation has been previously documented. Located in the intestinal crypts, stem cells constantly generate progeny that differentiate as they flow upward to the tip of the villi, where they die within days. TCF-mediated induction of c-Myc, with secondary induction of Ccnd1, is thought to drive proliferation in these cells and their malignant derivatives (Id.). Referring back to FIG. 5, normal appearing small intestine stained with pSmad3 shows identical staining pattern throughout the villi of both ApcMin/+; Tgfbr1+/+ mice (FIG. 5C) and ApcMin/+; Tgfbr1+/− mice (FIG. 5D); however, pSmad3 staining within the intestinal crypts of ApcMin/+; Tgfbr1+/− mice (arrow) is reduced when compared with that of their wild type counterparts (arrow). To assess the downstream effects of decreased Tgfbr1-mediated TGF-β signaling on Ccnd1 in vivo we measured the levels of Ccnd1 by IHC and found that Ccnd1 staining was significantly higher in the tumors of ApcMin/+; Tgfbr1+/− mice (50.7±4.1% positive staining) (FIG. 5D) than in those of ApcMin/+; Tgfbr1+/+ mice (20.1±5.7% positive staining) (FIG. 5C) (p=0.002).

To determine whether Tgfbr1 haploinsufficiency modifies tumor proliferation in vivo, the levels of proliferating cell nuclear antigen (PCNA) in tumors of ApcMin/+; Tgfbr1+/+ and ApcMin/+; Tgfbr1+/− mice were assessed. PCNA staining was significantly more intense in ApcMin/+; Tgfbr1+/− tumors (82.0±2.9% positive staining) than in their wild type counterpart (48.2±3.8% positive staining) (p=0.0003), thus establishing in vivo that decreased but not abrogated Tgfbr1-mediated signaling confers a selective growth advantage to tumor cells.

Example 8

Haploinsufficiency Inhibits the Development of Murine Mutant Kras-Induced Pancreatic Precancer Mice. EL-Kras transgenic and Tgfbr $1^{+/-}$ mice were generated as previously described in the art. EL-Kras FVB male mice were bred to Tgfbr $1^{+/-}$ C57/BL6 females.

Histology and immunohistochemistry. Mouse pancreas was stained with H&E and scored for the presence of pancreatic precancer. Incidence (mice with lesions/all mice), frequency (lesions/random section), size ($\mu m^2$) of the lesions, and accompanying phenotypic features were assessed.

Antibodies for immunohistochemistry included pSMAD2 and pSMAD3 antibodies (Cell Signaling), Smad4, Tgfbr1, Tgfbr1, and Tgfbr2 (Santa Cruz Biotechnology), cleaved caspase-3 (Cell Signaling), and bromodeoxyuridine (BrdUrd) antibody (Chemicon/Millipore). TUNEL staining was performed using an ApopTaq Peroxidase In situ Apoptosis Detection Kit (Millipore). pSmad2 and pSmad3 staining was graded on a 0 to 3+ scale in a blinded manner by two investigators (M. Sadim and P. J. Grippo). BrdUrd and TUNEL were calculated as percentages of positive nuclei/cells per total nucleated cells.

Western analysis. Protein lysates were loaded onto a gradient SDS-polyacrylamide gel and transferred to a polyvinylidene difluored Immobilon-P membrane (Millipore Corporation) which was blocked and incubated overnight with either Tgfbr1or Tgfbr2 antibodies. The secondary antibodies used were either horseradish peroxidase-linked antirabbit IgG (Cell Signaling Technology) or horseradish peroxidase-linked antimouse IgG (Cell Signaling Technology). Blots were visualized by Supersignal West Femto Maximum Sensitivity Substrate (Pierce) and densitometric scanning.

Statistics. Data were expressed as mean±SEM. Unpaired two-tailed t tests were used to anlyze differences in mouse lesion incidence, frequency, size, and BrdUrd and TUNEL counts. Analysis of pSMAD2 and pSMAD3 staining was performed with a Pearson $x^2$ analysis.

Tgfbr1 haploinsufficiency and pancreatic precancer. Upon histologic examination, we noted a general decrease in lipoatrophy, focal fibrosis, and lymphocytic infiltration in the haploinsufficient group. All 6-month-old EL-Kras mice have pancreatic precancer (unpublished findings from 75 mice). In this study, six out of six EL-Kras mice and three out of six EL-Kras/Tgfbr $1^{+/-}$ mice had precancerous lesions (P<0.05). There was also a significantly higher frequency of precancerous lesions found in EL-Kras compared with EL-Kras/Tgfbr $1^{+/-}$ mice (8.00±1.18 versus 1.50±0.67, respectively; P<0.0001). However, when EL-Kras/Tgfbr $1^{+/-}$ mice developed lesions, they were significantly larger than those seen in EL-Kras mice (4.522±1.417 versus 334±56 $\mu m^2$, respectively; P<0.01).

Effect of Tgfbr1 haploinsufficiency on precancerous cellular proliferation and apoptosis. We next sought to determine if the decrease in frequency and increase in size of precancerous lesions was the result of altered mitotic and/or apoptotic indices between Tgfbr1 haploinsufficent and control mice. The rate of BrdUrd incorporation (cell mitosis) was assessed in cells within precancerous lesions from EL-Kras and EL-Kras/Tgfbr $1^{+/-}$ mice. Immunohistochemistry for BrdUrd and TUNEL was scored as a percentage of positive nuclei/cells over total cells with nuclei per lesion per mouse.

There was a trend towards reduced proliferation in EL-Kras/Tgfbr1$^{+/-}$ mice compared with EL-Kras mice, which did not reach significant (7.65±1.097 versus 4.90±0.2034, respectively; P=0.067). The apoptotic rate of EL-Kras mice was significantly higher than that observed in EL-Kras/Tgfbr1$^{+/-}$ mice (8.036±0.5631 versus 2.368±0.5131; P<0.001), representing a nearly 3.5-fold difference. Samples were also stained with cleaved caspase-3 (data not shown) to verify TUNEL staining.

Analysis of Tgfbr1/Tgfbr2 ratio in whole mouse pancreas from EL-Kras/Tgfbr1$^{+/-}$ mice. Western analysis was used to determine the relative levels of Tgfbr1 compared with Tgfbr2. Immunohistochemical staining of precancerous lesions from EL-Kras and EL-Kras/Tgfbr1$^{+/-}$ mice displays a modest reduction in Tgfbr1 staining in precancerous lesions, although the change is quite subtle. Overall Tgfbr1 immunostaining of normal parenchyma was similar between the groups. Immunostaining for Tgfbr2 was modestly increased throughout the pancreas and focally increased in regions of precancerous lesions when comparing EL-Kras to EL-Kras/Tgfbr1$^{+/-}$ mice.

To establish a Tgfbr1/Tgfbr2 ratio, relative levels of Tgfbr1 (53 kDa) and Tgfbr2 (75 kDa) were determined in the same lane of total protein loaded. The average of each group (four mice) was compared with each other to show that the Tgfbr1/Tgfbr2 ratio for EL-Kras and EL-Kras/Tgfbr1$^{+/-}$ were 1:2 and 1:3, respectively. Interestingly, this reduction was not due to reduced Tgfbr1 but to increased Tgfbr2 in EL-Kras/Tgfbr1$^{+/-}$ mouse pancreas.

Downstream effects of Tgfbr1 haploinsufficency. Next, we sought to determine whether Tgfbr1 haploinsufficent mice had concomitant decreased levels of pSmad2 and pSmad 3 in pancreatic parenchyma and precancerous lesions. Using immunohistochemistry, we observed decreased staining in both the pancreatic parenchyma and precancerous lesions of EL-Kras/Tgfbr1$^{+/-}$ mice compared with EL-Kras mice. $X^2$ analysis of staining intensity for both pSmads showed a significantly stronger parenchymal staining in EL-Kras mice compared with EL-Kras/Tgfbr1$^{+/-}$ mice (P<0.01 and P<0.05, respectively). We observed Smad4 staining in pancreatic islets although with no detectable staining in exocrine tissues. The only difference was the presence of infrequent nuclear staining of islet cells in EL-Kras mice not observed in EL-Kras/Tgfbr1$^{+/-}$ mice.

The observation that TGFBR1 haploinsufficiency leads to a reduction of mutant Kras-derived preinvasive lesions of the pancreas supports the novel concept that a delicate balance in TGFB signaling between its cancer-suppressing and cancer-promiting attributes plays a central role in the early stages of precancer development. These findings also suggest that individuals with constitutively decreased TGFBR1 expression may have a lower risk for developing pancreatic cancer.

Example 8

Tgfbr1 Haplotype is Associated with Decreased Risk of Non-Small-Cell Lung Cancer (NSCLC)

Specimens. In case-control study 1, blood specimens were collected from 102 consecutive patients diagnosed with NSCLC at the First Affiliated Hospital of Soochow University. None of NSCLC patients had received either radiotherapy or chemotherapy before blood sampling. As controls, we collected blood samples from 104 geographically matched individuals with the same age range and without a history of cancer at the First Affiliated Hospital of Soochow University. In case-control study 2, blood specimens were collected from 131 patients with a diagnosis of NSCLC who had not received radiotherapy or chemotherapy and 133 geographically matched controls with the same age range at Wuxi Third People's Hospital.

Tagging SNP selection. HapMap SNP Phase II data7 were used to determine the frequency of SNPs among Han Chinese (CHB), and 74 SNPs were obtained from a 76-kb region of TGFBR1 from 28 kb upstream of the transcriptional start site to 7 kb downstream of the 3' untranslated region. Three haplotype blocks were reconstructed using these 74 SNPs with the Haploview program (Barrett J C, Fry B, Maller J, Daly M J. Haploview: analysis and visualization of LD and haplotype maps. Bioinformatics 2005; 21:263-5.). htSNP selection was done using the Haploview program. The Haploview program implemented a htSNP selection methodproposed by Carlson and colleagues (Carlson C S, Eberle M A, Rieder M J, Yi Q, Kruglyak L, Nickerson D A. Selecting a maximally informative set of single-nucleotide polymorphisms for association analyses using linkage disequilibrium. Am J Hum Genet 2004; 74:106-20), which selects a set of htSNPs such that each SNP considered has r2 greater than a prespecified threshold with at least one of the htSNPs. In our selection, only SNPs with minor allele frequency>10% were considered and the threshold of pairwise linkage disequilibrium (LD) was set as r 2=0.8. A total of seven htSNPs within three blocks were selected among 47 SNPs considered across TGFBR1, including three in the 5' flanking region, three in intronic regions, and one in the 3' flanking region. Genotyping. Genomic DNA from blood specimens was isolated according to standard proteinase K digestion and phenol-chloroform extraction. The seven TGFBR1 htSNPs were amplified by PCR. The PCR reaction was carried out in a total volume of 25 AL, containing 50 to 100 ng of genomic DNA, 1 unit of Ex Taq DNA polymerase (Takara, Japan), 0.2 Amol/L of each primer, 1 Ex Taq Buffer (Mg2+ Plus), 0.25 mmol/L of each deoxynucleotide triphosphate. Genotyping for the htSNPs was done by RFLP with restriction endonucleases. See Table 7. The different alleles were identified on a 2.5% agarose gel and visualized with ethidium bromide. See Table 6 for description of the SNPs. One htSNP (rs1888223) (chr9, position 100,904,795) was genotyped using SSCP because of lack of restriction endonuclease. For SSCP, the PCR products were mixed at 1:1 ratio with loading buffer (95% formamide, 0.05% xylene cyanol, and 0.05% bromophenol blue), denatured at 95 degree C. for 5 min, and cooled on ice for 2 min. Electrophoresis was done in 8% nondenaturing polyacrylamide gels and run at a constant 20 W for 5 h in 1 mM Tris-borate-EDTA running buffer, with the gel temperature maintained at 7 degree C. Ethidium bromide staining was used for detection of single-strand DNA in polyacrylamide gels. LD and haplotype analysis. Pairwise measures of LD measured by Lewontin coefficient (D') and squared correlation coefficient (r2) between the SNPs genotyped were calculated with the Haploview program. The frequencies of individual haplotypes were estimated from the genotype data using the SAS 9.1.3 PROC HAPLOTYPE and SHEsis programs (Shi YY, He L. SHEsis, a powerful software platform for analyses of linkage disequilibrium, haplotype construction, and genetic association at polymorphism loci. Cell Res 2005; 15:97-8.), which implement an expectation-maximization algorithm and a Full-Precise-Iteration algorithm for reconstructing haplotypes, respectively. Haplotypes with a frequency of <0.05 were not considered in the analysis. Logistic regression analysis was done using SAS PROC LOGISTIC to estimate the odds ratios (OR) and 95% confidence intervals (95% CI) of individual SNPs or haplotypes, with adjustment for age, sex, and smoking status. Statistical analysis. Two-sided m2 test or independent-samples t test was used to compare the difference in gender, age, and smoking status between NSCLC cases and controls. Hardy-Weinberg equilibrium analysis for genotype distribution in controls was carried out by a m2 goodness-of-fit test. Differences in genotype and allele frequencies between cases and controls were determined using m2 test. Logistic regression was done to assess OR and 95% CI, which were adjusted for gender, age, and smoking status. All the statistical analyses were implemented with SAS 9.1.3. Statistical significance cutoff was P<0.05. There was no significant difference with respect to sex and age between patients with NSCLC and controls (P<0.001 and P=0.006, respectively). The allele and genotype distributions for seven TGFBR1 htSNPs among NSCLC cases and controls are summarized in Table 2. The genotype frequencies of these polymorphisms were in Hardy-Weinberg equilibrium in controls in both studies. No significant difference in allele and genotype frequencies at any of these seven polymorphic sites was observed between NSCLC patients and controls in either study. D' value and r2 for these seven polymorphisms were calculated according to the genotyping data reported in Table 2. The different degrees of LD between cases and controls are summarized in Table 3. In case-control study 1, four polymorphisms consisting of rs10819638 (chr9, position 100,914,135), rs6478974(chr9, position 100,914,224), rs10733710(chr9, position 100,947, 245), and rs597457(chr9, position 100,957,611) were in LD with each other in cases (D'>0.8). In contrast, the D' values of rs107733710 with rs10819638 and rs6478974 and the D' value of rs6478974 with rs597457 were <0.80 in controls. Especially, LD between rs6478974 and rs10733710 was very weak in controls (D'=0.383, r2=0.014). Moreover, two htSNPs in the 5' flanking region, rs7040869 (chr9, position 100,874,969) and 4743325(chr9, position 100,895,548), had weaker LD in cases (D'=0.607, r2=0.111) than they had in controls (D'=0.848, r2=0.237). The LD findings in study 2 are similar to those in study 1 (Table 3). Accordingly, 4-SNP haplotypes (rs10819638, rs6478974, rs10733710, and rs597457) and 2-SNP haplotypes (rs7040869 and 4743325) were reconstructed according to the genotyping data in NSCLC patients and controls. Using haplotypes with frequencies of >0.05 for further analysis, four 4-SNP haplotypes accounted for 90.0% and 92.2% of the corresponding haplotypes in controls of study 1 and study 2, respectively; three 2-SNP haplotypes accounted for 98.1% and 97.5% of the corresponding haplotypes in controls of study 1 and study 2, respectively (Table 4). After adjustment for gender, age, and smoking status, a 4-SNP CTGC haplotype was significantly more common in controls than in cases in both casecontrol studies (P=0.014; adjusted OR, 0.09; 95% CI, 0.01-0.61; and P=0.010; adjusted OR, 0.11; 95% CI, 0.02-0.59, respectively) whereas the frequencies for all of 2-SNP haplotypes were not significantly different between NSCLC patients and controls. Moreover, as summarized in Table 5, combined analysis of both studies shows an association of this 4-SNP haplotype with decreased NSCLC risk (adjusted OR, 0.11; 95% CI, 0.03-0.39). Interestingly, four individuals were homozygous for the 4-SNP haplotype among controls (4 of 237) and none among cases (0 of 233; P=0.124). We did not observe any association between the 4-SNP haplotype and gender (P=0.745); age, assessed either as a categorical (P=0.584) or a continuous (P=0.317) variable; histology (P=0.599); and tumor-node-metastasis (TNM) stage (P=0.804). Importantly, we found that the pairwise LD values between these four SNPs were quite strong, especially for cases in both studies. These findings provide strong support for the novel notion that the CTGC haplotype is associated with lung cancer risk.

No significant differences in allele and genotype frequencies were observed between NSCLC patients and controls, which suggests that none of the individual TGFBR1 SNPs examined in this Example is associated with NSCLC risk. However, a 4-SNP TGFBR1 CTGC haplotype was significantly higher in controls (10.4% for study 1 and 8.8% for study 2) than in NSCLC patients (2.9% for study 1 and 3.1% for study 2), indicating that this haplotype may confer protection against NSCLC (combined adjusted OR, 0.11; 95% CI, 0.03-0.39).

Without being bound by theory, it is believed that constitutively decreased TGFBR1 signaling may be associated with increased cancer susceptibility that is not limited to colorectal cancer. Because of the observed protective effect of the TGFBR1 CTGC haplotype with respect to NSCLC risk, we predict that the CTGC haplotype is associated with increased TGF-β signaling.

Example 9

Generation of a Novel Mouse Model of Targeted Tgfbr1 Inactivation for Breast Cancer A knockout mouse model of TGFBR1 generated by targeted deletion of exon 3 has been previously described. There is growing evidence that the signal sequence of human TGFBR1*6A may have intrinsic biological effects, which are caused by mutations within the exon 1 GCG repeat sequence. While the exon 3 Tgfbr1 knockout model does not result in the generation of functional TGFBR1, the generation of a functionally active signal sequence cannot be excluded. To circumvent this potential problem, a classical knockout vector was designed to insert a Neomycin resistance cassette (Neo) into a Not I site located immediately after the start codon and removing 1.1 kb of mouse genomic sequence immediately upstream of this Not I site (FIG. 1A). This approach precludes the generation of any signal sequence, which is encoded by part of the removed sequence. The Tgfbr1+/− mice were viable and fertile, and appeared normal in their morphology and behavior. A total of 50 pups from the heterozygous intercrosses were genotyped, and no Tgfbr1−/− pups were found, with only the wild-types and the heterozygotes at the ratio of 1:2. Dead Tgfbr1−/− embryos were found at a ratio of 1:4 at the time of collection of MEFs. These findings are consistent with the previous report of targeted disruption of Tgfbr1 exon 3 in which mice lacking Tgfbr1 die at midgestation. Therefore, the stage of lethality was not determined. At 16-months, follow-up of 10 Tgfbr1+/− mice does not suggest increased mortality as compared with 10 wild-type littermates.

Tgfbr1 expression levels in different tissues were first compared by real-time PCR. Tgfbr1 expression in Tgfbr1+/− tissues ranged from 54% in embryonic fibroblasts to 62% in colonic epithelium, 44% in tail and 67% in blood lymphocytes when compared with corresponding expression levels in Tgfbr1+/+ mice (FIG. 1C). Tissue-specific differences between Tgfbr1+/− and Tgfbr1+/+ mice were significant for each corresponding tissue, p=0.016 for embryonic fibroblasts, p=0.04 for colonic epithelium, p=0.009 for tail, and p=0.01 for blood lymphocytes. The differences in Tgfbr1 expression levels between the various Tgfbr1+/− tissues were not statistically significant, p=0.429. To assess the functional consequences of Tgfbr1 haploinsufficiency we measured Tgfbr1 and Tgfbr2 protein expression in MEFs. Tgfbr1 expression levels were lower in the Tgfbr1+/− MEFs than in Tgfbr1+/+ MEFs.

Referring to FIG. 1D, Western blot analysis of Tgfbr1 and Tgfbr2 expression of two representative pairs of MEFs from Tgfbr1+/+ and Tgfbr1+/− mice is seen. As expected, Tgfbr2 levels were similar.

Tgfbr1 Haploinsufficiency Enhances Tumor Formation.

Figure 7:
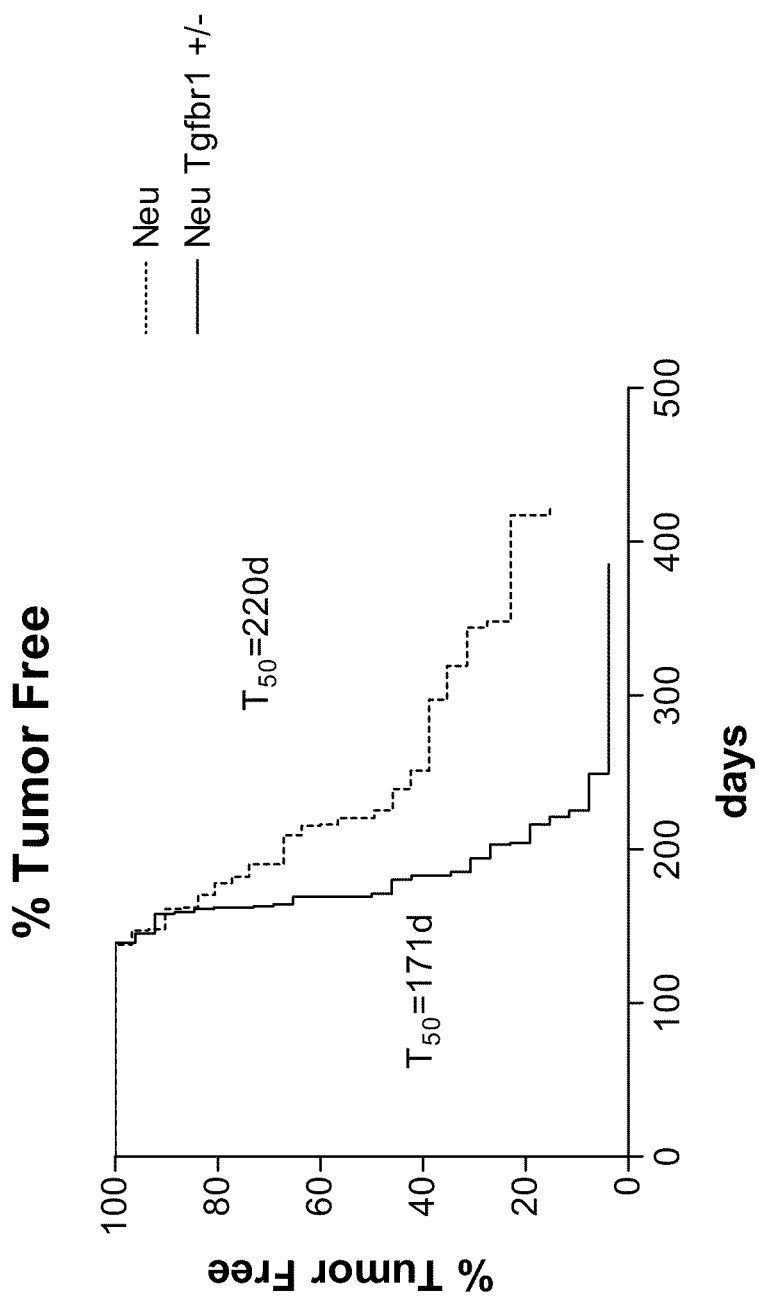
FIG. 7 shows tumorigenesis of Neu/+; Tgfbr1+/+ Neu/+; Tgfbr1+/− mice.
Figure 8:
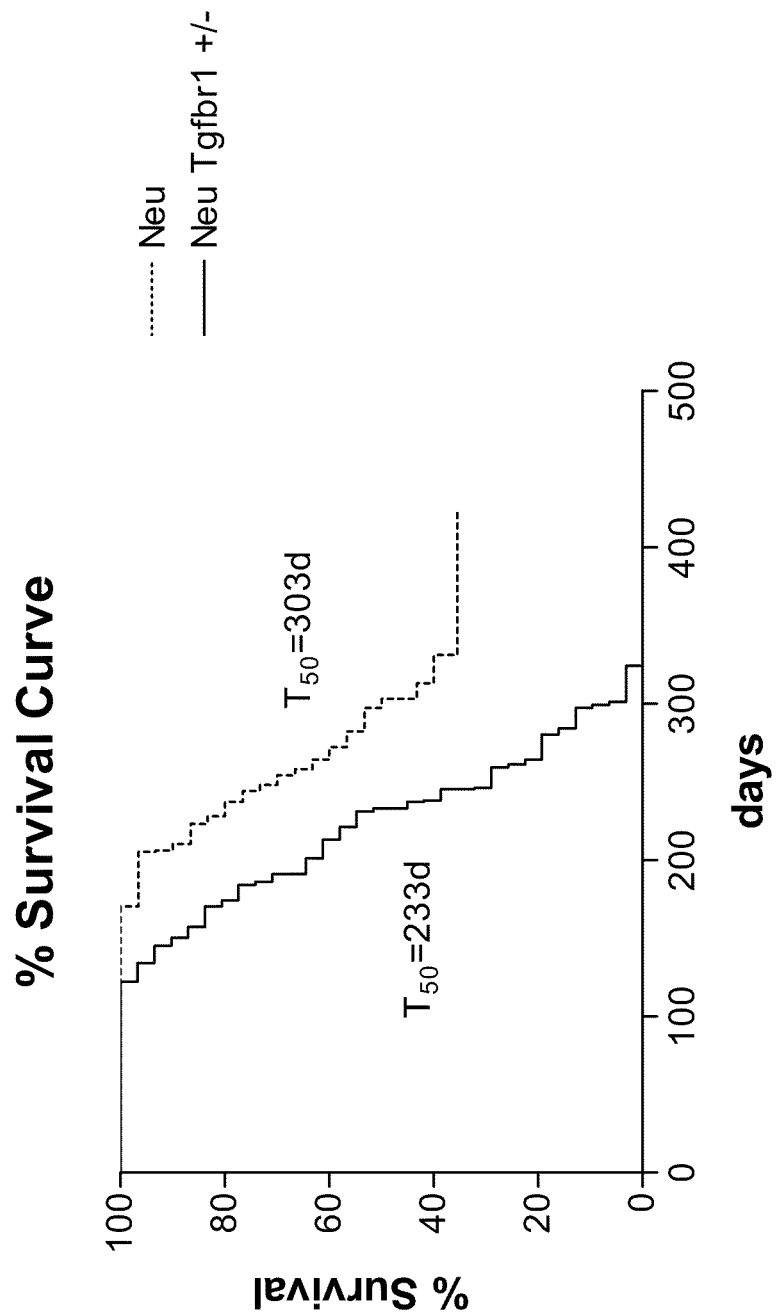
FIG. 8 shows survival of Neu/+; Tgfbr1+/+ Neu/+; Tgfbr1+/− mice.

The effect of Tgfbr1 haploinsufficiency on her2/neu/+-mediated breast cancer tumorigenesis was tested. HER2/neu (also known as ErbB-2, ERBB2) stands for "Human Epidermal growth factor Receptor 2" and is a protein giving higher aggressiveness in breast cancers. It is a member of the ErbB protein family, more commonly known as the epidermal growth factor receptor family. Female HER-2/neu transgenic mice develop spontaneous mammary tumors. Tgfbr1+/− female mice on the 129/SvIm background were backcrossed with HER-2/neu transgenic mice using standard methods as described elsewhere. The HER-2/Neu and HER-2/Neu Tgfbr1+/− mice were sacrificed at various times over 400+ days and examined for breast tumors. The tumors counted were verified by histology. Percent survival was tracked for a similar cohort of mice. Referring to FIG. 7, tumorigenesis of HER-2/Neu and HER-2/Neu; Tgfbr1+/− mice is seen. 26 HER-2/Neu; Tgfbr1+/− mice were used in the calculation and 31 Neu mice were used in the calculation. P=0.0004 Logrank Test, P=0.0234 t-test. Hazard ratio was 0.3937 and 95% CI was 0.1631-0.5975. The difference in number of tumors between the two groups was highly significant. FIG. 8 shows the percent survival curve of HER-2/Neu and HER-2/Neu; Tgfbr1+/− mice. 31 HER-2/Neu; Tgfbr1+/− mice were used in the calculation and 30 Neu mice were used in the calculation. P<0.0001 Logrank Test, Hazard ratio was 0.3027 and 95% CI was 0.1296-0.444. The difference in number of tumors between the two groups was highly significant.

While the invention has been described with specific embodiments, other alternatives, modifications, and variations will be apparent to those skilled in the art. Accordingly, it will be intended to include all such alternatives, modifications and variations set forth within the spirit and scope of the appended claims.

The following references are relevant for understanding the state of the art. The following reference list is not intended as an admission that any are pertinent prior art. All statements as to the date or representation as to the contents of these documents is based on the information available to the applicant and does not constitute any admission as to the correctness of the dates or contents of these documents.

(1) Howe J R, Sayed M G, Ahmed A F, Ringold J, Larsen-Haidle J, Merg A, et al. The prevalence of MADH4 and BMPR1A mutations in juvenile polyposis and absence of BMPR2, BMPR1B, and ACVR1 mutations. J Med Genet 2004 July; 41(7):484-91.

(2) Broderick P, Carvajal-Carmona L, Pittman A M, Webb E, Howarth K, Rowan A, et al. A genome-wide association study shows that common alleles of SMAD7 influence colorectal cancer risk. Nat Genet 2007 November; 39(11):1315-7.

(3) Xie W, Rimm D L, Lin Y, Shih W J, Reiss M. Loss of Smad signaling in human colorectal cancer is associated with advanced disease and poor prognosis. Cancer J 2003 July; 9(4):302-12.

(4) Sjoblom T, Jones S, Wood L D, Parsons D W, Lin J, Barber T D, et al. The Consensus Coding Sequences of Human Breast and Colorectal Cancers. Science 2006 Oct. 13; 314 (5797):268-74.

(5) Takaku K, Oshima M, Miyoshi H, Matsui M, Seldin M F, Taketo MM. Intestinal tumorigenesis in compound mutant mice of both dpc4 (Smad4) And apc genes. Cell 1998 Mar. 6; 92(5):645-56.

(6) Munoz N M, Upton M, Rojas A, Washington M K, Lin L, Chytil A, et al. Transforming Growth Factor {beta} Receptor Type II Inactivation Induces the Malignant Transformation of Intestinal Neoplasms Initiated by Apc Mutation. Cancer Res 2006 Oct. 15; 66(20):9837-44.

(7) Sodir N M, Chen X, Park R, Nickel A E, Conti P S, Moats R, et al. Smad3 Deficiency Promotes Tumorigenesis in the Distal Colon of ApcMin/+ Mice. Cancer Res 2006 Sep. 1; 66(17):8430-8.

(8) Kim B G, Li C, Qiao W, Mamura M, Kasperczak B, Anver M, et al. Smad4 signalling in T cells is required for suppression of gastrointestinal cancer. Nature 2006 Jun. 22; 441(7096):1015-9.

(9) Hohenstein P, Molenaar L, Elsing a J, Morreau H, van der K H, Struijk A, et al. Serrated adenomas and mixed polyposis caused by a splice acceptor deletion in the mouse Smad4 gene. Genes Chromosomes Cancer 2003 March; 36(3):273-82.

(10) Taketo M M, Takaku K. Gastro-intestinal tumorigenesis in Smad4 mutant mice. [Review] [41 refs]. Cytokine & Growth Factor Reviews 2000 March; 11(1-2):147-57.

(11) Alberici P, Jagmohan-Changur S, de P E, van d, V, Smits R, Hohenstein P, et al. Smad4 haploinsufficiency in mouse models for intestinal cancer. Oncog 2006 Mar. 23; 25(13):1841-51.

(12) Pasche B, Luo Y, Rao P H, Nimer S D, Dmitrovsky E, Caron P, et al. Type I transforming growth factor beta receptor maps to 9q22 and exhibits a 20 polymorphism and a rare variant within a polyalanine tract. Cancer Res 1998 Jul. 1; 58(13):2727-32.

(13) Chen T, de Vries E G, Hollema H, Yegen H A, Vellucci V F, Strickler H D, et al. Structural alterations of transforming growth factor-beta receptor genes in human cervical carcinoma. Int J Cancer 1999 Jul. 2; 82(1):43-51.

(14) Pasche B, Kolachana P, Nafa K, Satagopan J, Chen Y G, Lo R S, et al. T beta RI(6A) is a candidate tumor susceptibility allele. Cancer Res 1999 Nov. 15; 59(22):5678-82.

(15) Bian Y, Caldes T, Wijnen J, Franken P, Vasen H, Kaklamani V, et al. TGFBR1*6A May Contribute to Hereditary Colorectal Cancer. J Clin Oncol 2005 May 1; 23(13):3074-8.

(16) Xu Y, Pasche B. TGF-{beta} signaling alterations and susceptibility to colorectal cancer. Hum Mol Genet 2007 Apr. 15; 16 Spec No 1:R14-R20.

(17) Kaklamani V G, Baddi L, Liu J, Rosman D, Phukan S, Bradley C, et al. Combined Genetic Assessment of Transforming Growth Factor-{beta} Signaling Pathway Variants May Predict Breast Cancer Risk. Cancer Res 2005 Apr. 15; 65(8):3454-61.

(18) Valle L, Serena-Acedo T, Liyanarachchi S, Hampel H, Comeras I, Li Z, et al. Germline Allele-specific Expression of TGFBR1 Confers an Increased Risk of Colorectal Cancer. Science 2008 Aug. 14; 1159397.

(19) Hogan B, Beddington R, Costantini F, Lacy E. Manipulating the mouse embryo. 2nd ed. Cold Spring Harbor Laboratory Press; 1994.

(20) Tsutsui T, Hesabi B, Moons D S, Pandolfi P P, Hansel K S, Koff A, et al. Targeted disruption of CDK4 delays cell cycle entry with enhanced p27(Kip1) activity. Molecular & Cellular Biology 1999 October; 19(10):7011-9.

(21) Pasche B, Knobloch T J, Bian Y, Liu J, Phukan S, Rosman D, et al. Somatic Acquisition and Signaling of TGFBR1*6A in Cancer. JAMA: The Journal of the American Medical Association 2005 Oct. 5; 294(13):1634-46.

(22) Rosman D S, Phukan S, Huang C C, Pasche B. TGFBR1*6A Enhances the Migration and Invasion of MCF-7 Breast Cancer Cells through RhoA Activation. Cancer Res 2008 Mar. 1; 68(5):1319-28.
(23) Larsson J, Goumans M J, Sjostrand L J, van Rooijen M A, Ward D, Leveen, et al. Abnormal angiogenesis but intact hematopoietic potential in TGF-beta type I receptor-deficient mice. EMBO Journal 2001 Apr. 2; 20(7):1663-73.
(24) Moser A R, Pitot H C, Dove W F. A dominant mutation that predisposes to multiple intestinal neoplasia in the mouse. Science 1990 Jan. 19; 247(4940):322-4.21
(25) Su L K, Kinzler K W, Vogelstein B, Preisinger A C, Moser A R, Luongo C, et al. Multiple intestinal neoplasia caused by a mutation in the murine homolog of the APC gene. Science 1992 May 1; 256(5057):668-70.
(26) Carcamo J, Zentella A, Massague J. Disruption of transforming growth factor beta signaling by a mutation that prevents transphosphorylation within the receptor complex. Mol Cell Biol 1995; 15:1573-81.
(27) Zawel L, Dai J L, Buckhaults P, Zhou S, Kinzler K W, Vogelstein B, et al. Human Smad3 and Smad4 are sequence-specific transcription activators. Mol Cell 1998 March; 1(4):611-7.
(28) Dong M, Blobe G C. Role of transforming growth factor-beta in hematologic malignancies. Blood 2006 Jun. 15; 107(12):4589-96.
(29) Becker C, Fantini M C, Schramm C, Lehr H A, Wirtz S, Nikolaev A, et al. TGF-beta suppresses tumor progression in colon cancer by inhibition of IL-6 transsignaling. Immunity 2004 October; 21(4):491-501.
(30) Liu X D, Sun Y, Constantinescu S N, Karam E, Weinberg R A, Lodish H F. Transforming growth factor beta-induced phosphorylation of smad3 is required for growth inhibition and transcriptional induction in epithelial cells. Proc 1997 Sep. 30; 94(20):10669-74.
(31) Zhu Y A, Richardson J A, Parada L F, Graff J M. Smad3 mutant mice develop metastatic colorectal cancer. Cell 1998 Sep. 18; 94(6):703-14.
(32) Yamagata H, Matsuzaki K, Mori S, Yoshida K, Tahashi Y, Furukawa F, et al. Acceleration of Smad2 and Smad3 Phosphorylation via c-Jun NH2-Terminal Kinase during Human Colorectal Carcinogenesis. Cancer Res 2005 Jan. 1; 65(1):157-65.
(33) Matsuzaki K. Smad3 phosphoisoform-mediated signaling during sporadic human colorectal carcinogenesis. Histol Histopathol 2006 June; 21(6):645-62.
(34) Hulit J, Wang C, Li Z, Albanese C, Rao M, Di Vizio D, et al. Cyclin D1 Genetic Heterozygosity Regulates Colonic Epithelial Cell Differentiation and Tumor Number in Apc-Min Mice. Molecular and Cellular Biology 2004 Sep. 1; 24(17):7598-611.
(35) Van de W M, Sancho E, Verweij C, de Lau W, Oving I, Hurlstone A, et al. The beta-catenin/TCF-4 complex imposes a crypt progenitor phenotype on colorectal cancer cells. Cell 2002 Oct. 18; 111(2):241-50.
(36) Hinoi T, Akyol A, Theisen B K, Ferguson D O, Greenson J K, Williams B O, et al. Mouse Model of Colonic Adenoma-Carcinoma Progression Based on Somatic Apc Inactivation. Cancer Res 2007 Oct. 15; 67(20):9721-30.
(37) Boivin(*) G, double d, Yang([sect]) K, Ward(‖) J, Pretlow ([para]) T, Russell #, et al. Pathology of mouse models of intestinal cancer: Consensus report and recommendations. Gastroenterology 2003 March; 124(3):762-77.22
(38) Kitamura T, Kometani K, Hashida H, Matsunaga A, Miyoshi H, Hosogi H, et al. SMAD4-deficient intestinal tumors recruit CCR1+ myeloid cells that promote invasion. Nat Genet 2007 April; 39(4):467-75.
(39) Massague J. G1 cell-cycle control and cancer. Nature 2004 Nov. 18; 432(7015):298-306.
(40) Siegel P M, Massague J. Cytostatic and apoptotic actions of TGF-beta in homeostasis and cancer. Nat Rev Cancer 2003 November; 3(11):807-20.
(41) Groden J, Thliveris A, Samowitz W, Carlson M, Gelbert L, Albertsen H, et al. Identification and characterization of the familial adenomatous polyposis coli gene. Cell 1991 Aug. 9; 66(3):589-600.
(42) Kinzler K W, Vogelstein B. Landscaping the cancer terrain. Science 1998 May 15; 280(5366):1036-7.

TABLE 2

Genotype and allelic frequencies of TGFBR1 htSNPs among NSCLC cases and controls and associations with risk of NSCLC

| | Case-control study 1 | | | Case-control study 2 | | |
|---|---|---|---|---|---|---|
| | Cases/controls | OR (95% CI)* | P† | Cases/controls | OR (95% CI)* | P† |
| rs7040869 Genotype | | | | | | |
| GG | 57/58 | 1.00 | | 68/71 | 1.00 | |
| GA | 36/35 | 1.09 (0.58-2.03) | | 49/46 | 1.06 (0.62-1.80) | |
| AA | 9/11 | 0.96 (0.36-2.60) | 0.90 | 14/16 | 0.87 (0.39-1.97) | 0.87 |
| Allele | | | | | | |
| G | 150/151 | 1.00 | | 185/188 | 1.00 | |
| A | 54/57 | 0.95 (0.62-1.47) | 0.83 | 77/78 | 1.00 (0.69-1.46) | 0.99 |
| rs4743325 Genotype | | | | | | |
| TT | 31/30 | 1.00 | | 44/39 | 1.00 | |
| TG | 49/51 | 0.84 (0.43-1.64) | | 59/66 | 0.83 (0.47-1.47) | |
| GG | 22/23 | 0.71 (0.31-1.61) | 0.97 | 28/28 | 0.90 (0.45-1.79) | 0.71 |
| Allele | | | | | | |
| T | 111/111 | 1.00 | | 147/144 | 1.00 | |
| G | 93/97 | 0.96 (0.65-1.41) | 0.83 | 115/122 | 0.92 (0.66-1.30) | 0.65 |
| rs1888223 | | | | | | |

TABLE 2-continued

Genotype and allelic frequencies of TGFBR1 htSNPs among NSCLC cases and controls and associations with risk of NSCLC

| | Case-control study 1 | | | Case-control study 2 | | |
|---|---|---|---|---|---|---|
| | Cases/controls | OR (95% CI)* | P† | Cases/controls | OR (95% CI)* | P† |
| Genotype | | | | | | |
| AA | 31/28 | 1.00 | | 43/38 | 1.00 | |
| AC | 54/58 | 0.79 (0.41-1.53) | | 66/69 | 0.83 (0.47-1.46) | |
| CC | 17/18 | 0.70 (0.29-1.69) | 0.86 | 22/26 | 0.70 (0.34-1.45) | 0.71 |
| Allele | | | | | | |
| A | 116/114 | 1.00 | | 152/145 | 1.00 | |
| C | 88/94 | 0.92 (0.62-1.36) | 0.68 | 110/121 | 0.87 (0.62-1.22) | 0.42 |
| rs10819638 | | | | | | |
| Genotype | | | | | | |
| CC | 30/31 | 1.00 | | 45/43 | 1.00 | |
| CT | 53/57 | 0.86 (0.45-1.66) | | 61/68 | 0.84 (0.48-1.46) | |
| TT | 19/16 | 1.13 (0.48-2.71) | 0.82 | 25/22 | 0.98 (0.47-2.03) | 0.74 |
| Allele | | | | | | |
| C | 113/119 | 1.00 | | 151/154 | 1.00 | |
| T | 91/89 | 1.08 (0.73-1.59) | 0.71 | 111/112 | 1.01 (0.72-1.43) | 0.95 |
| rs6478974 | | | | | | |
| Genotype | | | | | | |
| TT | 40/38 | 1.00 | | 55/50 | 1.00 | |
| TA | 48/56 | 0.86 (0.46-1.59) | | 56/66 | 0.86 (0.51-1.48) | |
| AA | 14/10 | 1.18 (0.45-3.08) | 0.52 | 20/17 | 1.19 (0.55-2.58) | 0.53 |
| Allele | | | | | | |
| T | 128/132 | 1.00 | | 166/166 | 1.00 | |
| A | 76/76 | 1.03 (0.69-1.54) | 0.88 | 96/100 | 0.96 (0.67-1.37) | 0.82 |
| rs10733710 | | | | | | |
| Genotype | | | | | | |
| GG | 76/77 | 1.00 | | 89/98 | 1.00 | |
| GA | 20/24 | 0.78 (0.39-1.58) | | 36/31 | 1.21 (0.68-2.14) | |
| AA | 6/3 | 2.25 (0.52-9.99) | 0.51 | 6/4 | 1.49 (0.39-5.61) | 0.55 |
| Allele | | | | | | |
| G | 172/178 | 1.00 | | 214/227 | 1.00 | |
| A | 32/30 | 1.10 (0.64-1.90) | 0.72 | 48/39 | 1.30 (0.82-2.07) | 0.26 |
| rs597457 | | | | | | |
| Genotype | | | | | | |
| CC | 31/32 | 1.00 | | 45/43 | 1.00 | |
| CA | 51/52 | 0.92 (0.48-1.78) | | 60/65 | 0.89 (0.51-1.55) | |
| AA | 20/20 | 1.01 (0.44-2.32) | 1.00 | 26/25 | 0.90 (0.44-1.81) | 0.88 |
| Allele | | | | | | |
| C | 113/115 | 1.00 | | 150/151 | 1.00 | |
| A | 91/93 | 1.02 (0.69-1.50) | 0.94 | 112/115 | 0.98 (0.70-1.38) | 0.91 |

*Adjusted for age, gender, and smoking status.
†P value for $\chi^2$ analysis.

TABLE 3

D' and $r^2$ between pairs of seven TGFBR1 htSNPs in NSCLC cases and controls

| htSNP pairs | | Case-control study 1 | | Case-control study 2 | |
|---|---|---|---|---|---|
| | | D' Cases/controls | $r^2$ Cases/controls | D' Cases/controls | $r^2$ Cases/controls |
| rs7040869 | rs4743325 | 0.607/0.848 | 0.111/0.237 | 0.849/0.816 | 0.234/0.234 |
| rs7040869 | rs1888223 | 0.203/0.091 | 0.011/0.003 | 0.189/0.193 | 0.011/0.013 |
| rs7040869 | rs10819638 | 0.317/0.147 | 0.029/0.006 | 0.159/0.247 | 0.008/0.018 |
| rs7040869 | rs6478974 | 0.333/0.205 | 0.067/0.027 | 0.255/0.194 | 0.047/0.026 |
| rs7040869 | rs10733710 | 0.250/0.456 | 0.004/0.013 | 0.244/0.138 | 0.006/0.001 |
| rs7040869 | rs597457 | 0.342/0.045 | 0.034/0.001 | 0.239/0.205 | 0.018/0.013 |
| rs4743325 | rs1888223 | 0.042/0.087 | 0.002/0.007 | 0.151/0.045 | 0.021/0.002 |
| rs4743325 | rs10819638 | 0.124/0.174 | 0.015/0.026 | 0.211/0.157 | 0.042/0.021 |
| rs4743325 | rs6478974 | 0.070/0.210 | 0.002/0.022 | 0.381/0.113 | 0.066/0.007 |

TABLE 3-continued

D' and r² between pairs of seven TGFBR1 htSNPs in NSCLC cases and controls

| htSNP pairs | | Case-control study 1 | | Case-control study 2 | |
|---|---|---|---|---|---|
| | | D' Cases/controls | r² Cases/controls | D' Cases/controls | r² Cases/controls |
| rs4743325 | rs10733710 | 0.008/0.269 | 0.000/0.014 | 0.064/0.101 | 0.001/0.002 |
| rs4743325 | rs597457 | 0.170/0.004 | 0.028/0.000 | 0.223/0.042 | 0.047/0.002 |
| rs1888223 | rs10819638 | 0.754/0.799 | 0.536/0.579 | 0.818/0.841 | 0.658/0.616 |
| rs1888223 | rs6478974 | 0.784/0.884 | 0.227/0.371 | 0.968/0.889 | 0.392/0.397 |
| rs1888223 | rs10733710 | 1.000/0.783 | 0.141/0.085 | 1.000/0.742 | 0.162/0.079 |
| rs1888223 | rs597457 | 0.755/0.618 | 0.537/0.368 | 0.833/0.718 | 0.673/0.470 |
| rs10819638 | rs6478974 | 1.000/0.916 | 0.478/0.361 | 1.000/0.938 | 0.425/0.386 |
| rs10819638 | rs10733710 | 1.000/0.759 | 0.150/0.073 | 0.920/0.791 | 0.140/0.078 |
| rs10819638 | rs597457 | 0.980/0.851 | 0.961/0.682 | 0.968/0.885 | 0.923/0.748 |
| rs6478974 | rs10733710 | 0.889/0.383 | 0.087/0.014 | 0.902/0.608 | 0.105/0.038 |
| rs6478974 | rs597457 | 0.963/0.709 | 0.443/0.229 | 0.970/0.817 | 0.406/0.307 |
| rs10733710 | rs597457 | 1.000/0.883 | 0.150/0.104 | 0.922/0.899 | 0.142/0.106 |

NOTE:
Values of D' and r² were calculated with the Haploview program.

TABLE 4

Frequencies of estimated 4-SNP and 2-SNP haplotypes of TGFBR1 in NSCLC cases and controls

| | 4-SNP haplotype* | | | | 2-SNP haplotype* | | |
|---|---|---|---|---|---|---|---|
| | TTGA | CAGC | CTAC | CTGC | GG | GT | AT |
| Case-control study 1 | | | | | | | |
| Cases (%)/controls (%) | 44.1/38.6 | 36.3/29.2 | 15.2/11.8 | 2.9/10.4 | 40.8/44.7 | 32.7/27.9 | 21.7/25.5 |
| Crude OR (95% CI)† | 1.08 (0.72-1.61) | 1.21 (0.80-1.85) | 1.20 (0.68-2.13) | 0.24 (0.09-0.60) | 0.90 (0.60-1.33) | 1.31 (0.86-2.00) | 0.84 (0.53-1.33) |
| P | 0.707 | 0.365 | 0.526 | 0.001 | 0.588 | 0.291 | 0.464 |
| Adjusted OR (95% CI)‡ | 1.48 (0.64-3.42) | 1.88 (0.76-4.63) | 1.80 (0.60-5.37) | 0.09 (0.01-0.61) | 0.59 (0.26-1.31) | 1.81 (0.74-4.39) | 0.83 (0.32-2.18) |
| P | 0.363 | 0.171 | 0.293 | 0.014 | 0.195 | 0.191 | 0.706 |
| Case-control study 2 | | | | | | | |
| Cases (%)/controls (%) | 41.6/38.8 | 35.9/31.9 | 17.2/12.7 | 3.1/8.8 | 41.9/43.4 | 28.7/27.3 | 27.4/26.8 |
| Crude OR (95% CI)† | 1.02 (0.72-1.45) | 1.10 (0.76-1.58) | 1.34 (0.82-2.17) | 0.31 (0.14-0.70) | 0.93 (0.66-1.32) | 1.06 (0.73-1.56) | 1.02 (0.70-1.50) |
| P | 0.911 | 0.626 | 0.239 | 0.003 | 0.695 | 0.752 | 0.908 |
| Adjusted OR (95% CI)‡ | 1.16 (0.58-2.34) | 1.66 (0.78-3.53) | 1.94 (0.74-5.12) | 0.11 (0.02-0.59) | 0.93 (0.47-1.84) | 1.19 (0.54-2.63) | 1.00 (0.47-2.15) |
| P | 0.679 | 0.185 | 0.181 | 0.01 | 0.823 | 0.668 | 0.993 |

NOTE:
Haplotypes with frequencies of >5% were included.
*Four htSNPs alleles from left to right (i.e., rs10819638, rs6478974, rs10733710, and rs597457) and two htSNPs (rs7040869 and rs4743325) were used for 4-SNP and 2-SNP reconstruction of haplotypes. Haplotype bases are depicted from the coding strand of TGFBR1.
†Calculated with SHEsis program.
‡Adjusted for gender, age, and smoking status using SAS software.

TABLE 5

Frequencies of estimated 4-SNP and 2-SNP haplotypes of TGFBR1 in combined cases and controls

| | Combined case-control study | | | | | |
|---|---|---|---|---|---|---|
| Haplotype* | Cases (%) | Controls (%) | Crude OR (95% CI)† | P | Adjusted OR (95% CI)‡ | P |
| 4-SNP | | | | | | |
| TTGA | 42.7 | 38.7 | 1.05 (0.80-1.36) | 0.736 | 1.24 (0.72-2.12) | 0.440 |
| CAGC | 36.0 | 30.7 | 1.14 (0.87-1.51) | 0.338 | 1.64 (0.93-2.90) | 0.090 |

TABLE 5-continued

Frequencies of estimated 4-SNP and 2-SNP haplotypes of TGFBR1 in combined cases and controls

| Haplotype* | Combined case-control study | | | | | |
|---|---|---|---|---|---|---|
| | Cases (%) | Controls (%) | Crude OR (95% CI)† | P | Adjusted OR (95% CI)‡ | P |
| CTAC | 16.3 | 12.3 | 1.28 (0.88-1.85) | 0.193 | 2.07 (1.00-4.28) | 0.050 |
| CTGC | 3.0 | 9.5 | 0.27 (0.15-0.51) | 0.00001 | 0.11 (0.03-0.39) | 0.0007 |
| 2-SNP | | | | | | |
| GG | 41.5 | 44.0 | 0.92 (0.71-1.19) | 0.521 | 0.78 (0.47-1.31) | 0.348 |
| GT | 30.4 | 27.6 | 1.16 (0.88-1.54) | 0.298 | 1.43 (0.80-2.58) | 0.230 |
| AT | 25.0 | 26.2 | 0.95 (0.71-1.27) | 0.722 | 0.91 (0.50-1.66) | 0.767 |

NOTE:
Haplotypes with frequencies of >5% were included.
*Four htSNPs alleles from left to right (i.e., rs10819638, rs6478974, rs10733710, and rs597457) and two htSNPs (rs7040869 and rs4743325) were used for 4-SNP and 2-SNP reconstruction of haplotypes. Haplotype bases are depicted from the coding strand of TGFBR1.
†Calculated with SHEsis program.
‡Adjusted for gender, age, and smoking status using SAS software.

TABLE 6

Haplotype tagging SNPs* of the TGFBR1 gene in the Chinese population

| SNP | ID | Chromosome position | Location in gene | Base change† | Minor allele (frequency) |
|---|---|---|---|---|---|
| SNP1 | rs7040869 | 100874968 | 5'-flanking | G > A | A (0.344) |
| SNP2 | rs4743325 | 100889547 | 5'-flanking | G > T | G (0.356) |
| SNP3 | rs1888223 | 100904795 | 5'-flanking | C/A | C (0.456) |
| SNP4 | rs10819638 | 100914135 | intron 1 | C > T | T (0.489) |
| SNP5 | rs6478974 | 100914224 | intron 1 | T > A | A (0.322) |
| SNP6 | rs10733710 | 100947245 | intron 6 | G > A | A (0.144) |
| SNP7 | rs597457 | 100957611 | 3'-flanking | A > C | A (0.489) |

*SNP position and minor allele frequency are based on the NCBI dbSNP Build 129 (http://www.ncbi.nih.gov/SNP).
†We present C/A for the rs1888223 polymorphism as its ancestral allele is not available in the NCBI dbSNP database.

TABLE 7

Primers and restriction endonucleases used for TGFBR1 genotyping

| htSNP ID | Primer sequences* | | Tm (° C.) | Product length (bp) | Restriction endonuclease | Incubation temperature (° C.) | Specific allele (position)‡ |
|---|---|---|---|---|---|---|---|
| rs7040869 | FP: | ACATAGAGTAGACCGAAGA | 53 | 439 | Pvu II | 37 | G (177) |
| | RP: | AGAAGCAAGACAGATAGAC | | | | | |
| rs4743325 | FP: | GCCATTTTCTCCTCCACA | 55 | 335 | Hinc II | 37 | G (90) |
| | RP: | CCAAAGGGCTCATCAAAG | | | | | |
| rs1888223 | FP: | ATAGTGTTCCCAGACCCA | 55 | 223 | — | — | — |
| | RP: | GCATTTGTAATAGACATCCC | | | | | |
| rs10819638 | FP: | GGAAAAGTAAGAGGCAGTCTTGC | 60 | 361 | Bsm I | 37 | C (206) |
| | RP: | TAGCCACCCTGATCCATTCC | | | | | |
| rs6478974 | FP: | GGAAAAGTAAGAGGCAGTCTTGC | 60 | 361 | Hph I | 37 | T (306) |
| | RP: | TAGCCACCCTGATCCATTCC | | | | | |
| rs10733710 | FP: | CCTGCTGATGAAAGGTTG | 57 | 295 | Acl I | 37 | G (71) |
| | RP: | CTACGGGAAAGGTGGGT | | | | | |

TABLE 7-continued

Primers and restriction endonucleases used for TGFBR1 genotyping

| htSNP ID | Primer sequences* | Tm (° C.) | Product length (bp) | Restriction endonuclease | Incubation temperature (° C.) | Specific allele (position)‡ |
|---|---|---|---|---|---|---|
| rs597457 | FP: AACATGCAAACAGTAATCGT RP: TTCTTTTGTATGCCTGTGAT | 53 | 273 | Rsa I | 37 | C (46) |

*FP, Forward primer; RP, Reverse primer.
†rs1888223 was genotyped using SSCP.
‡The polymorphic alleles are identified following cleavage by restriction endonucleases, which yield fragments of different sizes for the different alleles.

What is claimed is:

1. A method for treatment of colorectal cancer in a human individual, the method comprising the steps of:
   (a) obtaining a sample of peripheral blood from the individual;
   (b) determining the expression level of TGFBR1 in the sample obtained from the individual;
   (c) obtaining a reference expression level for TGFBR1 for a normal control;
   (d) comparing the expression level for TGFBR1 of step (b) with the reference expression level for TGFBR1 of step (c),
   (e) determining that the individual has an increased susceptibility to colorectal cancer wherein a ratio of the sample expression level of TGFBR1 to the reference expression level of TGFBR1 indicates lowered expression level of TGFBR1 in the sample;
   (f) providing colonoscopy to the individual with increased susceptibility to colorectal cancer to determine if the individual has colorectal cancer; and
   (g) treating the individual with radiotherapy or chemotherapy if the individual has colorectal cancer.

* * * * *

SEQUENCE LISTING

<160> NUMBER OF SEQ ID NOS: 19

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
agaccccagc tcttagcccc ca    22

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
gagacgctcc acccaccttc cc    22

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
gaagctgact ctagaggatc cc    22

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
ttccactttg gcataaggc    19

<210> SEQ ID NO 5
<211> LENGTH: 21
<212> TYPE: DNA
<213> ORGANISM: Artificial Sequence
<220> FEATURE:
<223> OTHER INFORMATION: Synthetic

```
<400> SEQUENCE: 5
ttctgagaaa gacagaagtt a                                                 21

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
acatagagta gaccgaaga                                                    19

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
agaagcaaga cagatagac                                                    19

<210> SEQ ID NO 8
<211> LENGTH: 18
<212> TYPE: DNA
<213> ORGANISM: Artificial Sequence
<220> FEATURE:
<223> OTHER INFORMATION: Synthetic

<400> SEQUENCE: 8
gccattttct cctccaca                                                     18

<210> SEQ ID NO 9
<211> LENGTH: 18
<212> TYPE: DNA
<213> ORGANISM: Artificial Sequence
<220> FEATURE:
<223> OTHER INFORMATION: Synthetic

<400> SEQUENCE: 9
ccaaagggct catcaaag                                                     18

<210> SEQ ID NO 10
<211> LENGTH: 18
<212> TYPE: DNA
<213> ORGANISM: Artificial Sequence
<220> FEATURE:
<223> OTHER INFORMATION: Synthetic

<400> SEQUENCE: 10
atagtgttcc cagaccca                                                     18

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
gcatttgtaa tagacatccc                                                   20

<210> SEQ ID NO 12
<211> LENGTH: 23
<212> TYPE: DNA
```

```
<213> ORGANISM: Artificial Sequence
<220> FEATURE:
<223> OTHER INFORMATION: Synthetic

<400> SEQUENCE: 12
ggaaaagtaa gaggcagtct tgc                                              23

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
tagccaccct gatccattcc                                                  20

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
ggaaaagtaa gaggcagtct tgc                                              23

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
tagccaccct gatccattcc                                                  20

<210> SEQ ID NO 16
<211> LENGTH: 18
<212> TYPE: DNA
<213> ORGANISM: Artificial Sequence
<220> FEATURE:
<223> OTHER INFORMATION: Synthetic

<400> SEQUENCE: 16
cctgctgatg aaaggttg                                                    18

<210> SEQ ID NO 17
<211> LENGTH: 17
<212> TYPE: DNA
<213> ORGANISM: Artificial Sequence
<220> FEATURE:
<223> OTHER INFORMATION: Synthetic

<400> SEQUENCE: 17
ctacgggaaa ggtgggt                                                     17

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
aacatgcaaa cagtaatcgt                                                  20
```

```
<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ttcttttgta tgcctgtgat                                              20
```